United States Patent
Kuzmich et al.

(10) Patent No.: US 10,343,974 B1
(45) Date of Patent: Jul. 9, 2019

(54) CYCLOHEXANOL ETHERS AS MEDITERRANEAN FRUIT FLY ATTRACTANTS

(71) Applicant: The United States of America, as Represented by the Secretary of Agriculture, Washington, DC (US)

(72) Inventors: Daniel Kuzmich, Clovis, CA (US); Spencer S. Walse, Fresno, CA (US)

(73) Assignee: The United States of America, as represented by The Secretary of America, Washington, DC (US)

( * ) Notice: Subject to any disclaimer, the term of this patent is extended or adjusted under 35 U.S.C. 154(b) by 0 days.

(21) Appl. No.: 16/101,805

(22) Filed: Aug. 13, 2018

(51) Int. Cl.
  *C07C 69/92* (2006.01)
  *A01N 37/40* (2006.01)
  *C07C 67/333* (2006.01)

(52) U.S. Cl.
  CPC .............. *C07C 69/92* (2013.01); *A01N 37/40* (2013.01); *C07C 67/333* (2013.01); *C07C 2601/14* (2017.05)

(58) Field of Classification Search
  CPC ... C07C 69/92; C07C 2601/14; C07C 67/333; A01N 37/40
  See application file for complete search history.

(56) References Cited

U.S. PATENT DOCUMENTS 6,375,943 B1   4/2002   Raw et al.

OTHER PUBLICATIONS

Khrimian, A. et al., "A practical synthesis of ceralure B1, a potent attractant for the Mediterranean fruit fly," Proceedings of the 6th International Fruit Fly Symposium, (2002), pp. 279-282.
Khrimian, A. et al., "An improved synthesis of ethyl cis-5-iodo-trans-2-methylcyclohexanecarboxylate, a potent attractant for the Mediterranean fruit fly," Science Direct: Tetrahedron, (2003), 59:5475-5480.
Demilo, A. B. et al., "Trimedlure: Effects of Structural Modifications on Its Attractiveness to Mediterranean Fruit Fly Males (Diptera: Tephritidae)," Journal of Economic Entomology, (1994), 87(6):1494-1501.
Jang, Eric B. et al., "Field Response of Mediterranean Fruit Fly (Diptera: Tephritidae) to Ceralure B1: Evaluations of enantiomeric B1 Ratios on Fly Captures," J. Econ. Entomol, (2005), 98(4):1139-1143.
Avery, James W. et al., "Regioselective Synthesis of Ceralure B1 and A, Ethyl cis-(and tram-) 5-Iodo-~runs=2~Methylcyclahexane-1-Carboxylate," Tetrahedron Letters, (1994), 35(50):9337-9338.
Beroza, Morton et al., "New Attractants for the Mediterranean Fruit Fly," Ag and Food chemistry, (1961), 9(5):361-365.
McGovern, T.P. et al., "Attraction of Mediterranean Fruit Flies (Diptera: Tephritidae) to Analogs of Selected Trimedlure Isomers1," J. Econ. Entomol., (1988), 81(4):1052-1056.
Gow, Paul L. et al., "Proteinaceous Bait for the Oriental Fruit Fly," J. Econ. Entomol., (1954), 47(1):153-160.
Vargas, Roger I. et al., "Suppression of Mediterranean Fruit Fly (Diptera: Tephritidae) With Trimedlure and Biolure Dispensers in Coffea arabica (Gentianales: Rubiaceae) in Hawaii," Journal of Economic Tntomology, (2018), 111(1):293-297.
Demilo, A.B. et al., "Trimedlure:Effects of Structural Modifications on Its Attractiveness to Mediterranean Fruit Fly Males (Diptera: Tephritidae)", Ecology and Behavior, (1994), 87(6):1494-1501.

*Primary Examiner* — Yevgeny Valenrod
*Assistant Examiner* — Blaine G Doletski
(74) *Attorney, Agent, or Firm* — John D. Fado; Ediz Yonter; Gail E. Poulos

(57) ABSTRACT

Disclosed are novel cyclohexanol ethers of Formula (I) useful as Mediterranean fruit fly, *Ceratitas capitata*, attractants:

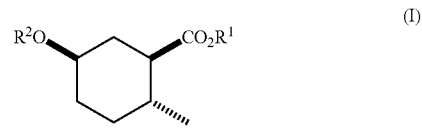

(I)

wherein $R^1$ is $C_{1-5}$ alkyl optionally substituted with 0-3 halogens, and $R^2$ is $C_{1-3}$ alkyl. Also disclosed are methods of preparation, methods of formulation, and methods of use.

15 Claims, No Drawings

CYCLOHEXANOL ETHERS AS MEDITERRANEAN FRUIT FLY ATTRACTANTS

FIELD OF THE INVENTION

The present invention relates generally to novel cyclohexanol ethers that are useful as attractants for the Mediterranean fruit fly, Ceratitas capitata. The invention also relates to methods of preparation, methods of formulation, and methods of use.

BACKGROUND OF THE INVENTION

The Mediterranean fruit fly (medfly), Ceratitas capitata (Wiedemann), is a serious agricultural pest worldwide. Found in tropical/sub-tropical areas and established in Hawaii, it is a frequent invader of Florida, Texas, and California. The establishment of medfly in these regions of the continental United States poses a serious threat to horticultural production and trade, and results in an increased use of pesticides. Outbreaks of medfly in most agriculturally important regions of the United States are regulated with quarantines that trigger massive eradication and detection procedures to minimize potential damage to commercially valuable host fruit (USDA, APHIS, Fruit Fly Exclusion and Detection Programs 2011, Exotic Fruit Fly Strategic Plan FY2011-2015).

Maintaining a medfly-free continental United States has relied heavily on monitoring with an extensive network of trapping systems that employ chemical attractants. Currently, traps for male medfly utilize a synthetic lure trimedlure (TML), which is a mixture of 16 regio- and stereoisomers of tert-butyl esters of 4 (and 5)-chloro-2-methylcyclohexane-1-carboxylate (Beroza, M., et al., J. Agric. Food Chem., 9: 361 (1961)). Although classified as a weak attractant, TML has been in use for over 50 years while the development of more potent attractants, such as α-copaene—a host volatile (Flath, R. A., et al., J. Chem. Ecol., 10: 2595 (1994)) and ceralure (ethyl esters of 4 (and 5)-iodo-2-methylcyclohexane-1-carboxylate) (Warthen, J. D., et al., J. Chem. Ecol., 24: 1305 (1998))—a TML analog, have not been adopted due to the high economic costs of their synthesis (Tan, K. H., et al., Pheromones, Male Lures, and Trapping of Tephritid Fruit Flies, Epsky, N. D., et al., History and Development of Food-Based Attractants, IN: Trapping and the Detection, Control, and Regulation of Tephritid Fruit Flies: Lures, Area-Wide Programs, and Trade Implications, Shelly, T., et al., Eds., Springer: Dordrecht, 2014, pp. 15-118). TML is typically dispensed as a "gummy" containing 2 grams of attractant formulated in a polymer matrix. Over 1 million "gummies" are produced and sold annually for use as attractants in detection traps.

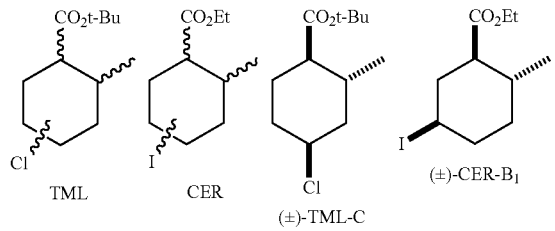

TML   CER   (±)-TML-C   (±)-CER-B$_1$

Several analogs of TML have been reported, however much of the structure-activity-relationship (SAR) stems, curiously, from bioassays involving isomeric mixtures (De-Milo A. B., et al., J. Econ. Entomol., 87: 1494 (1994); McGovern, T. P., et al., J. Econ. Entomol., 81: 1052 (1988)). Ceralure (CER), the iodo analog of TML, emerged from these SAR efforts. Commercial CER is also as a mixture of 16 regio- and stereoisomers of 4 (and 5)-iodo-2-methylcyclohexane-1-carboxylate. The isomeric components of commercially prepared TML and CER have been separated, at considerable effort, and their relative attractiveness has been established in bioassays. The most potent isomer of commercially available preparations of TML and CER have been identified as TML-C and CER-B$_1$, respectively. While there are no reports of a stereoselective synthesis of TML-C, considerable effort has been directed towards the synthesis of the more potent isomers of commercial CER due to the improved efficacy of CER relative to TML and CER-B$_1$ relative to TML-C (Warthen, J. D., et al., J. Chem. Ecol., 20: 569 (1994); Jang, E., et al., J. Econ. Entomol., 103: 1586 (2010)). An enantioselective synthesis of CER-B$_1$ (Khrimian, A., et al., Tetrahedron, 59: 5475 (2003)) and a regioselective synthesis that yields only two CER isomers, CER-B$_1$ and CER-A (Avery, J. W., et al., Tetrahedron Letters, 35: 9337 (1994); Khrimian, A., et al., Proceedings of 6$^{th}$ International Fruit Fly Symposium Stellenbosch, South Africa 279 (2002)) has been reported. Unfortunately, further refinement in the preparation of CER or CER-B$_1$ have not been forthcoming and existing procedures for the synthesis of enriched mixtures of CER-B$_1$ are economically unfavorable and are not suitable for industrial production since they are inefficient, difficult to scale-up, require tedious purification steps, and use toxic and costly reagents. Indeed, to our knowledge, no efficient preparations of CER-B$_1$ has been developed that justify the use of CER over the commercially available mixture of TML isomers. Moreover, CER is known to be unstable in formulations and the environment (DeMilo, A. B., Ceralure, IN: USDA-ARS Action Plan for Fruit Flies Research, Faust, R. M.; Coppedge, J. R. Eds., U.S. Department of Agriculture, Agricultural Research Service, 1992, pp. 11).

The isomeric composition of TML influences attractiveness, and in turn, the efficiency of monitoring programs. To ensure consistent efficacy, the USDA Animal and Plant Health Inspection Service (APHIS) requires a certificate of analysis that TML must contain a minimum of 38% of trans-C isomer, no more than 24% of B$_2$-isomer, and no more than 10% of cis-TML (total of 4 isomers). The development of commercial TML as a mixture of 8 diastereomers has placed an undue burden on the synthetic process, quality control, and the ability to accurately study TML in the laboratory and field.

Novel diastereomically pure compounds useful as medfly attractants would therefor constitute an advantage over the state of the art (TML and/or CER) by simplifying synthetic preparation, eliminating mixtures that complicate quality control, and increasing environmental stability. Herein we report such compounds.

SUMMARY OF THE INVENTION

Disclosed are novel diastereomically pure cyclohexanol ethers that are useful for attracting medfly. Also disclosed are methods of preparation, methods of formulation, and methods of use. In all schemes, unless specified otherwise, R$^1$ and R$^2$ in the formulas and schemes have the meanings of R$^1$ and R$^2$ disclosed in the Summary of the Invention section.

In the broadest generic aspect, there are disclosed compounds of Formula (I)

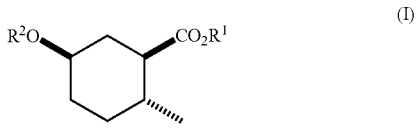

(I)

wherein $R^1$ is $C_{1-5}$ alkyl optionally substituted with 0-3 halogens, and $R^2$ is $C_{1-3}$ alkyl.

Also disclosed are compounds of Formula (I) wherein $R^1$ is methyl, ethyl, n-propyl, isopropyl, —$CH_2CF_3$, sec-butyl, tert-butyl, and $R^2$ is methyl.

Furthermore, there are disclosed compounds of Formula (I) wherein $R^1$ is ethyl, isopropyl, —$CH_2CF_3$, and $R^2$ is methyl.

The following are representative compounds of the invention that can be made according to the general schemes and specific examples disclosed herein and methods known in the art. A compound of Formula (I) in the table below may be used as an attractant for medfly, said compound having the relative stereochemistry depicted in the table below unless noted otherwise. In the event that the structures of compounds disclosed herein are in conflict with the nomenclature, then the compounds are defined by their structure.

| Structure | Name | Data[a] |
|---|---|---|
| 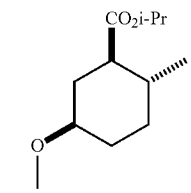 | (1R*,2R*,5R*)-isopropyl 5-methoxy-2-methylcyclohexanecarboxylate | IR (neat) 2978, 1728, 1101 $cm^{-1}$; $^1H$ NMR (300 MHz, $CDCl_3$) δ 5.02 (hept, J = 6.2 Hz, 1H), 3.34 (s, 3H), 3.13 (m, 1H), 2.18 (m, 1H), 2.04 (m, 1H), 1.95 (m, 1H), 1.78 (m, 1H), 1.66 (m, 1H), 1.47-1.31 (m, 1H), 1.31-1.15 (m, partially obscured by doublets at 1.24 and 1.22 ppm, 1H), 1.23 (d, J = 6.3 Hz, 3H), 1.22 (d, J = 6.3 Hz, 3H), 0.88 (d, J = 6.4 Hz, 3H); $^{13}C$ NMR (75 MHz, $CDCl_3$) δ 174.10, 78.21, 67.08, 55.50, 49.64, 34.57, 33.72, 32.22, 31.38, 21.64, 21.53, 19.43; GC-EIMS m/z (% rel. abundance) 214 (8), 184 (31). |
| 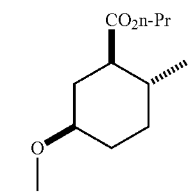 | (1R*,2R*,5R*)-propyl 5-methoxy-2-methylcyclohexanecarboxylate | IR (neat) 2934, 1732, 1100 $cm^{-1}$; $^1H$ NMR (300 MHz, $CDCl_3$) δ 4.04 (td, J = 6.6, 0.7 Hz, 2H), 3.34 (s, 3H), 3.21-3.05 (m, 1H), 2.20 (ddd, J = 12.1, 6.1, 3.7 Hz, 1H), 2.11-1.92 (m, 2H), 1.78 (dq, J = 13.4, 3.5 Hz, 1H), 1.72-1.63 (m, 3H), 1.39 (td, J = 12.4, 11.2 Hz, 1H), 1.33-1.15 (m, 1H), 1.13-0.99 (m, 1H), 0.94 (t, J = 7.4 Hz, 3H), 0.89 (d, J = 6.4 Hz, 3H); $^{13}C$ NMR (75 MHz, $CDCl_3$) δ 174.69, 78.21, 65.60, 55.51, 49.58, 34.65, 33.77, 32.23, 31.39, 21.87, 19.55, 10.23; GC-EIMS m/z (% rel. abundance) 214 (7), 184 (36). |
| 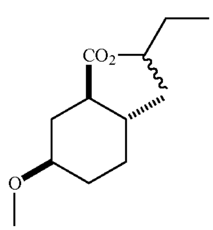 | (1R*,2R*,5R*)-sec-butyl 5-methoxy-2-methylcyclohexanecarboxylate | IR (neat) 2933, 1727, 1099 $cm^{-1}$; $^1H$ NMR (300 MHz, $CDCl_3$) δ 4.85 (q, J = 6.2 Hz, 1H), 3.34 (s, 3H), 3.22-3.05 (m, 1H), 2.23-2.13 (m, 1H), 2.09-1.90 (m, 2H), 1.83-1.72 (m, 1H), 1.72-1.46 (m, 3H), 1.46-1.32 (m, 1H), 1.31-1.22 (m, 1H), 1.19 and 1.18 (overlapping doublets due to racemic methyl group of the 2-methyl propyl group, J = 6.3 Hz, 3H), 1.11-0.94 (m, 1H), 0.92-0.86 (m, 6H); $^{13}C$ NMR (75 MHz, $CDCl_3$) δ 174.00, 173.96, 78.08, 78.06, 71.46, 71.44, 55.31, 55.29, 49.71, 49.64, 34.65, 34.58, 33.61, 33.49, 32.10, 32.06, 31.26, 31.22, 28.49, 19.34, 19.21, 19.10, 9.41, 9.37 (doubling of some peaks is due to diastereomers due to the sec-butyl group); GC-EIMS m/z (% rel. abundance) 228 (6), 198 (8), 155 (36), 95 (100). |
| 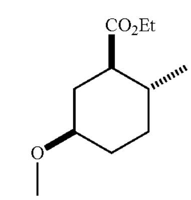 | (1R*,2R*,5R*)-ethyl 5-methoxy-2-methylcyclohexanecarboxylate | IR (neat) 2932, 1729, 1177, 1138, 1097 $cm^{-1}$; $^1H$ NMR (300 MHz, $CDCl_3$) δ 4.07 (q, J = 15.0, 6.0 Hz, 2H), 3.26 (s, 3H), 3.12-2.99 (m, 1H), 2.16-2.07 (m, 1H), 2.01-1.86 (m, 2H), 1.77-1.66 (m, 1H), 1.64-1.50 (m, 1H), 1.37-1.23 (m, 1H), 1.18 (t, J = 7.1 Hz, 4H), 1.04-0.88 (m, 1H), 0.81 (d, J = 6.4 Hz, 3H); $^{13}C$ NMR (75 MHz, $CDCl_3$) δ 174.92, 78.39, 60.18, 55.75, 49.66, 34.71, 33.92, 32.39, 31.57, 19.70, 14.26; GC-EIMS m/z (% rel. abundance) 200.1 (8), 170 (63). |

-continued

| Structure | Name | Data[a] |
|---|---|---|
| (structure: CO₂t-Bu cyclohexane with OMe) | (1R*,2R*,5R*)-tert-butyl 5-methoxy-2-methylcyclohexanecarboxylate | IR (neat) cm$^{-1}$ 2931, 1724, 1155, 1138, 1099; $^1$H NMR (300 MHz, CDCl$_3$) δ 3.34 (s, 3H), 3.18-3.05 (m, 1H), 2.23-2.13 (m, 1H), 2.09-1.96 (m, 1H), 1.86 (ddd, J = 12.6, 10.9, 3.3 Hz, 1H), 1.76 (dq, J = 13.4, 3.5 Hz, 1H), 1.68-1.53 (m, 1H), 1.44 (s, 9H), 1.41-1.30 (m, 1H), 1.30-1.20 (m, 1H), 1.10-0.97 (m, 1H), 0.89 (d, J = 6.4 Hz, 3H); $^{13}$C NMR (75 MHz, CDCl$_3$) δ 174.27, 80.01, 78.45, 77.58, 77.16, 76.73, 55.75, 50.67, 34.83, 33.97, 32.37, 31.58, 28.03, 19.62. |
| (structure: CO₂CH₂CF₃ cyclohexane with OMe) | (1R*,2R*,5R*)-2,2,2-trifluoroethyl 5-methoxy-2-methylcyclohexanecarboxylate | IR (neat) cm$^{-1}$ 2934, 1752, 1272, 1127, 1098; $^1$H NMR (300 MHz, CDCl$_3$) δ 4.48 (q, J = 8.5 Hz, 2H), 3.34 (s, 3H), 3.14 (ddd, J = 15.0, 10.9, 4.0 Hz, 1H), 2.27-2.17 (m, 1H), 2.17-1.98 (m, 2H), 1.80 (dt, J = 13.3, 3.5 Hz, 1H), 1.75-1.61 (m, 1H), 1.41 (q, J= 12.0 Hz, 1H), 1.34-1.17 (m, 1H), 1.14-0.96 (m, 1H), 0.89 (d, J = 6.4 Hz, 3H); $^{13}$C NMR (75 MHz, CDCl$_3$) δ 173.29, 123.03 (q, J = 277.2 Hz), 78.16, 60.78, 60.29, 59.81, 59.32, 55.85, 49.21, 34.56, 33.92, 32.29, 31.45, 19.57; GC-EIMS m/z (% rel. abundance) 254 (3), 224 (41), 198 (48). |

(a) See Synthetic Examples Section for m.p., IR, NMR, GC-MS instrumentation and methods.

This summary is provided to introduce a selection of concepts in a simplified form that are further described below in the detailed description. This summary is not intended to identify key features or essential features of the claimed subject matter, nor is it intended as an aid in determining the scope of the claimed subject matter.

DETAILED DESCRIPTION OF THE INVENTION

Definition of Terms and Conventions Used: Unless defined otherwise, all technical and scientific terms used herein have the same meaning as commonly understood by one of ordinary skill in the art to which the invention belongs. Other more specific definitions are as follows:

The terms "alkyl" or "alkyl group" mean a branched or straight-chain saturated aliphatic hydrocarbon monovalent radical. This term is exemplified by groups such as methyl, ethyl, n-propyl (n-Pr), 1-methylethyl (iso-propyl or i-Pr), 1-methylpropyl (sec-butyl or s-Bu), and the like.

The terms "halogen" or "halo" shall be understood to mean fluorine, bromine, chlorine, or iodine.

Compounds of the invention also include their isotopically-labelled forms. Deuterium labelled compounds of Formula (I) can be prepared according to known methods using commercially available deuterium labelled reagents such as iodomethane-d$_3$ in place of iodomethane.

Optimum reaction conditions, which may include the stoichiometry of reactants and reaction times, may vary depending on the particular reactants used. Unless otherwise specified, reagents, solvents, temperatures, pressure, and other reaction conditions may be readily selected by one of ordinary skill in the art given the teaching of this application. For example, selected solvents in the General Synthetic Methods or Synthetic Examples section does not exclude the selection of another solvent known to those skilled in the art for conducting similar synthetic transformations.

Amounts, percentages, and ranges are not meant to be limiting, and increments between the recited amounts, percentages, and ranges are specifically envisioned as part of the invention. All ranges and parameters disclosed herein are understood to encompass any and all sub-ranges subsumed therein, and every number between the endpoints. For example, a stated range of "1 to 10" should be considered to include any and all subranges between (and inclusive of) the minimum value of 1 and the maximum value of 10 including all integer values and decimal values; that is, all subranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

General Synthetic Methods: The present invention provides for methods for making compounds of Formula (I). The compounds of the invention may be prepared by the general methods and examples presented below, and methods known to those of ordinary skill in the art and reported in the literature. Specific procedures are provided in the Synthetic Examples section.

Siglure acid of Formula (IV) is either commercially available or prepared according to the method of Diels and Alder (Diels, O. and Alder, K., Liebigs Ann., 470: 62 (1929)) by modified general methods known to those skilled in the art. Iodolactone (V) is prepared according to known methods and may be prepared from siglure acid according to known or general procedures, or prepared by one skilled in the art (House, H. O., et al., J. Org. Chem., 48:1643 (1983); Avery, J. W., et al., Tetrahedron Lett., 35: 9337 (1994); Khrimian, A., et al., Tetrahedron, 59: 5475 (2003)). Hydrodehalogenation of iodolactone (V) or iodo compounds of Formula (VI) can be accomplished according to known methods (Mandal, P. K., et al., J. Org. Chem., 79: 8422 (2014); U.S. Pat. No. 6,375,943). Lactone (Formula VIII) can be ring-opened according to known methods using a sodium or potassium alkoxide, generated for example from ethanol and sodium hydride, or reacting the lactone with ethanol in the presence of K$_2$CO$_3$. Lactone (Formula V) can be ring-opened using a suitable alcohol and catalytic acid such as ethanolic-HCl. Synthetic intermediates useful in the synthesis of compounds of Formula (I), prepared by general methods and exemplified below, also constitute part of the invention.

Compounds of Formula (I) with various $R_1$ and $R_2$ substitution, may be prepared according to Scheme I:

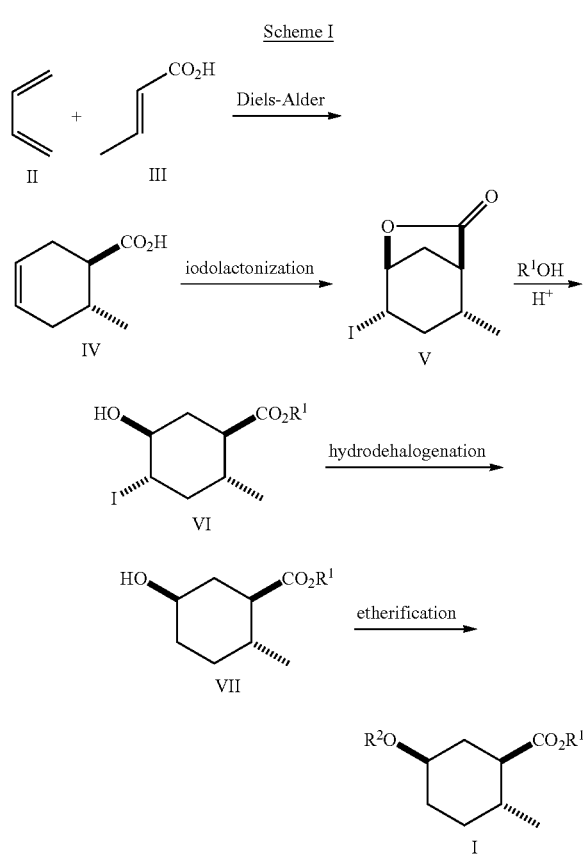

As illustrated in Scheme I, 1,3-butadiene of Formula (II) is reacted with (E)-crotonic acid (III) to form siglure acid (IV). Iodolactonization of the compound of Formula (IV) with KI, iodine and $NaHCO_3$ in water and optionally a suitable ether co-solvent or chlorinated co-solvent (e.g., tetrahydrofuran, diethyl ether or dichloromethane) affords the iodolactone of Formula (V). Ring-opening of the compound of Formula (V) with a primary alcohol (e.g., methanol, ethanol or n-propanol) in the presence of a catalytic acid (e.g., HCl or p-TsOH·$H_2O$) provides an ester of Formula (VI). Reduction of the compound of Formula (VI) in a suitable polar solvent (e.g., ethyl acetate (EtOAc) or ethanol (EtOH)) using a suitable catalyst (e.g., palladium on carbon, platinum oxide (Adam's catalyst), Raney nickel, or palladium hydroxide) in the presence of hydrogen at a suitable pressure (e.g., about 1 to about 7 atmospheres) and an amine base (e.g., triethylamine, N,N-diisopropylethylamine (DIEA) or pyridine) forms the compound of Formula (VII). Etherification of the compound of Formula (VII) in a suitable polar aprotic solvent (e.g., dimethylformamide (DMF) or acetonitrile) using a combination of an alkyl halide (e.g., iodomethane) and a suitable base (e.g., NaH) or silver (I) oxide provides a compound of Formula (I) where $R^2$ is methyl.

An alternate method for preparing compounds of Formula (I) may be prepared according to Scheme II:

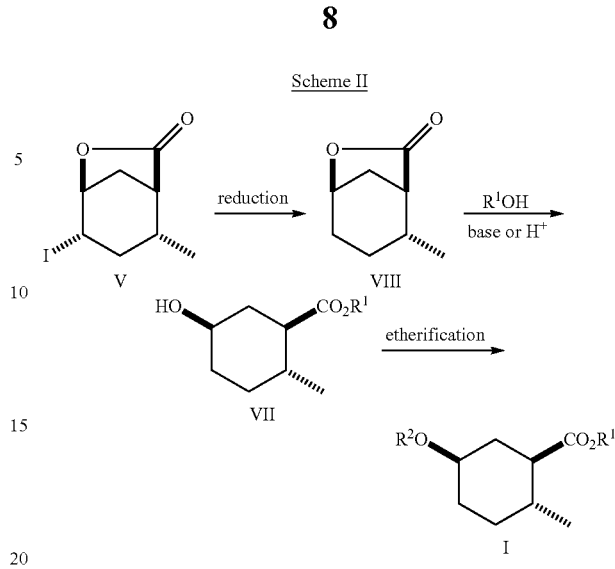

As illustrated in Scheme II, iodolactone of Formula (V) is reduced under hydrogenation conditions in a suitable polar solvent (e.g., ethyl acetate or ethanol) using a suitable catalyst (e.g., palladium on carbon, platinum oxide (Adam's catalyst), palladium hydroxide or Raney® nickel) in the presence of hydrogen at a suitable pressure (1-7 atmospheres) and an amine base (e.g., triethylamine, DIEA or pyridine) to afford the lactone of Formula (VIII). Alternatively, iodolactone of Formula (V) is reduced using tri-n-butyl tin hydride and a radical initiator (e.g., azobisisobutyronitrile (AIBN)) to afford the lactone of Formula (VIII). Ring-opening of the lactone with an alcohol (e.g., ethanol, propanol isopropanol, (±)-2-butanol (sec-butylalcohol) and the like) in the presence of a suitable base (e.g., NaH or $K_2CO_3$) or a suitable acid such as HCl (g) (e.g., ethanolic-HCl) provides an ester of Formula (VII). Etherification as described in Scheme I affords a cyclohexanol ether of Formula (I).

Yet another method for preparing compounds of Formula (I) may be accomplished according to Scheme III:

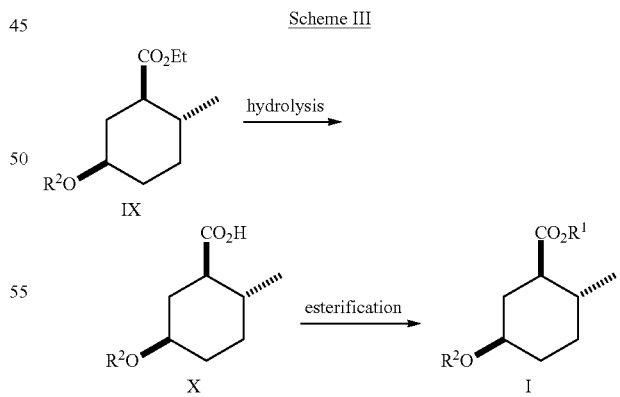

As illustrated in Scheme III, an ester of Formula (IX) is hydrolyzed under basic conditions in water and a suitable alcoholic co-solvent (e.g., methanol or ethanol) using a suitable base (e.g., sodium, potassium or lithium hydroxide) to afford a carboxylic acid of Formula (X). Treatment of the carboxylic acid of Formula (X) with $SOCl_2$ or oxalyl chloride-DMF followed by an alcohol (e.g., propanol, isopropanol, (±)-2-butanol (sec-butyl alcohol), 2,2,2-trifluoroethanol and the like) in the presence of a suitable base (e.g., pyridine) affords a compound of Formula (I). Treatment of the carboxylic acid of Formula (X) with isobutylene in the presence of an acid catalyst (e.g., sulfuric acid) affords an ester of Formula (I) where $R^1$ is tert-butyl.

Isomers are defined as diastereomers or enantiomers. Each stereocenter may be in the R or S configuration or a combination of configurations. All isomeric forms of the compounds of Formula (I) are included in the invention. For example, enantiomers of compounds of Formula (I) may be prepared from chiral siglure acid (IV) (Clive, D. L. J., et al., J. Am. Chem. Soc., 112: 3018 (1990)) or by the chiral resolution of diastereomeric esters or amides prepared from compounds of Formula (X) and a chiral resolution agent (e.g., (1S,2R,5S)-(+)-menthol, (S)-(−)-α-methylbenzylamine or the like).

The compounds described herein (useful, for example, in attracting medfly) may be applied with a carrier component or carrier (e.g., agronomically or physiologically or pharmaceutically acceptable carrier). The carrier component can be a liquid or a solid material. As is known in the art, the vehicle or carrier to be used refers to a substrate such as a membrane, hollow fiber, microcapsule, cigarette filter, gel, polymers, bags, vials, septa, or the like. All of these substrates have been used to release volatile chemicals in general and are well known in the art. Suitable carriers are well-known in the art and are selected in accordance with the ultimate application of interest. Agronomically acceptable substances include aqueous solutions, oils, glycols, alcohols, ketones, esters, hydrocarbons, halogenated hydrocarbons, polyvinyl chloride; in addition, solid carriers such as clays, cellulosic, fibers, and rubber materials and synthetic polymers. The carrier or carrier material as used herein is defined as not including the body of an insect (e.g., medfly).

The amount of the composition for attracting medfly will be at least an effective amount (i.e., 1 mg or more). The term "effective amount," as used herein, means the minimum amount of the composition needed to attract medfly to a treated area or object or locus when compared to the same area or object or locus which is untreated. Of course, the precise amount needed will vary in accordance with the particular composition used; the type of area or object to be treated; the number of days of attractiveness needed; and the environment in which the area or object or locus is located. The precise amount of the composition can easily be determined by one skilled in the art given the teaching of this application. For example, one skilled in the art could follow the procedures utilized below; the composition would be statistically significant in comparison to a control (e.g., water). Generally, the concentrations of synthetic chemicals discussed herein on polypropylene flex tube or plastic bag would range from about 10 mg to about 4000 mg (e.g., 10 to 4000 mg), monitoring traps would generally use about 2000 mg while attract and kill may use about 3000 mg (e.g., 3000 mg), and release amounts could generally be about 0.05 to about 100 mg (e.g., 0.05 to 100 mg) per tube/bag per day. The release rate of compositions described herein can be determined by methods known in the art and would be expected to vary depending upon chemical structure, physical properties (i.e., vapor pressure, boiling point and the like) and environmental conditions (i.e., temperature).

The compositions described herein may or may not contain a control agent for medfly, such as a biological control agent or an insecticide known in the art to kill medfly. Other compounds may be added to the composition provided they do not substantially interfere with the intended activity of the composition; whether or not a compound interferes with attractant activity can be determined, for example, by the procedures utilized below.

"Optional" or "optionally" means that the subsequently described event or circumstance may or may not occur, and that the description includes instances in which said event or circumstance occurs and instances where it does not. For example, the phrase "optionally comprising an insecticide" means that the composition may or may not contain an insecticide and that this description includes compositions that contain and do not contain an insecticide.

Unless defined otherwise, all technical and scientific terms used herein have the same meaning as commonly understood by one of ordinary skill in the art to which the invention belongs. Unless otherwise indicated, all numbers expressing quantities of ingredients, properties such as molecular weight, reaction conditions (e.g., reaction time, temperature), percentages and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. As used herein, the term "about" refers to a quantity, level, value, or amount that varies by as much as 10% to a reference quantity, level, value, or amount.

Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Instrumentation and Methods: Reactions requiring an inert atmosphere were conducted under nitrogen in commercially available (Aldrich) dry solvents unless noted otherwise. All reactions were conducted at room temperature unless noted otherwise. All reactions were brought to room temperature prior to workup unless noted otherwise. Typically, reaction monitoring was performed by thin-layer chromatography on Analtech or E-Merck silica gel TLC plates or by gas chromatography-electron impact mass spectrometry (GC-EIMS). Developed plates were visualized using phosphomolybdic acid (PMA) stain. Typically, intermediates and products were purified by flash chromatography using 230-400 mesh Merck silica gel or pre-packed silica gel cartridges from Silicycle or by recrystallization or distillation. All compounds were characterized by at least one of the following methods: $^1$H or $^{13}$C NMR, IR, GC-MS or melting point. Melting points were recorded on a Stuart SMP30 and are uncorrected. Infrared spectra were recorded on a Nicolet iS10 Fourier Transform Infrared Spectrometer. Samples were analyzed as films applied to the instrument in volatile solvents and are reported as wavenumber (cm$^{-1}$). $^1$H and $^{13}$C NMR spectra were recorded on a Bruker Fourier 300 NMR spectrometer. Chemical shifts (δ) were reported as the shift in parts per million (ppm) from internal deuterated solvent, CDCl$_3$ at 7.26 for proton and 77.16 ppm for carbon, respectively. $^1$H spectra data were reported as follows: chemical shift; number of protons; multiplicity (s) singlet, (d) doublet, (t) triplet, (q) quartet, (qu) quintet, (m) multiplet; (b) broad, D$_2$O exchangeable; coupling constants (J) in hertz. Carbon spectral data were reported as follows: chemical shift (δ) and assignment (multiplicity determined using DEPT experiments). Mass spectra were recorded on a 7890A gas chromatograph and a 5975C quadrupole mass spectrometer or a 6890 gas chromatograph and a 5973N quadrupole mass spectrometer (Agilent Technologies, Santa Clara, Calif.) operated with electron impact (EI) ionization (70 eV). Cool on-column injections (~1 μL) were at 143° C. with He carrier gas (1.0 mL min$^{-1}$). The oven program methods were optimized for the compounds of interest (a general method for example was as follows: isothermal at 60° C. for 1 min, heated at 10° C. min$^{-1}$ to 240° C., isothermal for 11 min. GlasSeal connectors (Supleco®, Milwaukee, Wis.) fused four columns in series; a deactivated column (L=8 cm, ID=0.53 mm) (Agilent Technologies, Santa Clara, Calif.: No. 160-2535-10) onto which the injection was deposited, a deactivated retention-gap column (L=2 m, ID=0.25 mm) (Agilent Technologies, Santa Clara, Calif.: No. 160-2255-30), a DB-1701 analytical column (L=60 m, ID=0.25 mm, df=0.25 μm) (J&W Santa Clara, Calif.: part #122-0762), and finally a deactivated column (L=1.5 m, ID=0.25 mm) (Agilent Technologies, Santa Clara, Calif.: No. 160-2255-30) that was directed into the detector. Transfer-line, source, and quadrupole temperatures were respectively 280, 230, and 150° C. Full scan spectra (m/z 50 to 600) with ±0.3 m/z resolution were acquired at 0.34 s per scan for qualitative verification. Mass spectral data were reported as mass-to-charge ratios (m/z) and relative intensity (% of base peak). All stereochemical depictions were in the relative sense unless otherwise noted. The following are representative examples that illustrate the processes of the invention.

SYNTHETIC EXAMPLES

Example 1: Synthesis of (1R*,2R*,5R*)-ethyl 5-methoxy-2-methylcyclohexanecarboxylate (1)

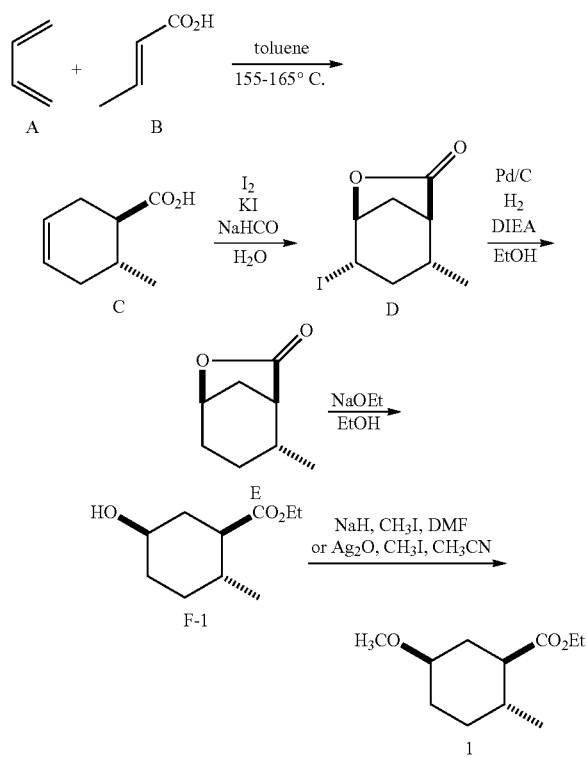

(1R*,6R*)-6-methylcyclohex-3-enecarboxylic acid (C, siglure acid) was prepared according to the method of Diels and Alder (1929). A 100-mL stainless steel Parr pressure flask was charged with a 20% solution of 1,3-butadiene (A) in toluene (55.0 mL, 164 mmol), crotonic acid (B) (17.0 g, 197 mmol) and galvinoxyl (56 mg, 0.13 mmol), and warmed at 182° C. After 6 h, the reaction was cooled to room temperature, the pressure flask was vented and opened. The reaction was diluted with hexanes (150 mL) and extracted with aqueous $K_2CO_3$ (40 g in 3×150 mL). The combined basic aqueous layers were washed with EtOAc (3×50 mL), made acidic (pH 2) with 12 N aq HCl, and chilled with crushed ice. The solid was collected by filtration washing with cold water and dried by pulling vacuum through the filter cake to afford siglure acid (C) as a white solid: $^1$H NMR (300 MHz, CDCl$_3$) δ 5.69-5.64 (m, 2H), 2.42-2.24 (m, 3H), 2.24-2.11 (m, 1H), 2.06-1.86 (m, 1H), 1.83-1.64 (m, 1H), 1.03 (d, J=6.5 Hz, 2H).

To a suspension of siglure acid (C) (15.4 g, 110 mmol) in water (150 mL) was added in several portions NaHCO$_3$ (28.4 g, 338 mmol) followed by KI (21.5 g, 129 mmol) and $I_2$ (32.0 g, 126 mmol). After 18 h, sodium sulfite (4.5 g) and ether (50 mL) was added. The ether layer was then concentrated in vacuo to afford a solid. The solid was collected by filtration washing with cold water and dried by pulling vacuum through the filter cake. The tan solid was dissolved in $CH_2Cl_2$ and passed through a short pad of silica gel. The material from the pad was recrystallized from $CH_2Cl_2$-ether-hexanes to afford (1S*,4S*,5S*)-4-iodo-6-oxa-bicyclo[3.2.1]octan-7-one (D) as white needles: m.p. 92.5-95.6° C.; $^1$H NMR (300 MHz, Chloroform-d) δ 4.87 (dd, J=5.8, 3.7 Hz, 1H), 4.43-4.33 (m, 1H), 2.92 (d, J=12.7 Hz, 1H), 2.69 (dt, J=16.8, 7.0 Hz, 1H), 2.57-2.47 (m, 1H), 2.43-2.31 (m, 1H), 2.33-2.18 (m, 1H), 1.99 (d, J=16.8 Hz, 1H), 1.40 (d, J=7.3 Hz, 3H).

A solution of (1S*,4S*,5S*)-4-iodo-6-oxa-bicyclo[3.2.1]octan-7-one (D) (1.064 g, 3.999 mmol), DIEA (1.0 mL, 5.7 mmol) and 10% palladium on carbon (100 mg) in EtOH (10 mL) was placed under 80 psi of hydrogen. After 18 h, the reaction was filtered through Celite®, washed with ethyl acetate, and concentrated. The residue was diluted with saturated aqueous NH$_4$Cl (30 mL) and extracted with ethyl acetate (3×25 mL). The organic layers were combined, washed with brine (3×15 mL), dried (MgSO$_4$), filtered and concentrated to afford (1S*,5R*)-6-oxa-bicyclo[3.2.1]octan-7-one (E).

To a solution of absolute ethanol (100 mL) was added 60% NaH (2.4 g, 60 mmol) in mineral oil in several portions. After H$_2$ evolution ceased, (1S*,5R*)-6-oxa-bicyclo[3.2.1]octan-7-one (E) (5.6 g, 40 mmol) was added in one portion. After 2 h, the reaction was diluted with saturated aqueous NH$_4$Cl (150 mL) and concentrated to remove excess ethanol. The remaining aqueous layer was extracted with methyl tert-butylether (MTBE) (3×75 mL). The organic layers were combined, washed consecutively with saturated aqueous NH$_4$Cl (100 mL) then water (3×100 mL), then brine (100 mL), dried (MgSO$_4$), filtered and concentrated. The crude material was dissolved in hexanes and purified by silica gel chromatography, eluting with a gradient of 0-30% EtOAc in hexanes to afford (1R*,2R*,5R*)-ethyl 5-hydroxy-2-methylcyclohexanecarboxylate (F-1).

The following intermediates were prepared from (1S*,4S*,5S*)-4-iodo-6-oxa-bicyclo[3.2.1]octan-7-one according to the method described in example 1 with the following modifications: ethanol is replaced with isopropanol to afford:

(1R*,2R*,5R*)-isopropyl 5-hydroxy-2-methylcyclohexanecarboxylate (F-2): IR (neat) 3392 (broad), 2931, 1726, 1708, 1106 cm$^{-1}$; $^1$H NMR (300 MHz, CDCl$_3$) δ (hept, J=6.3 Hz, 1H), 3.47 (m, 1H), 3.03 (br, 1H), 1.95 (m, 1H), 1.91-1.79 (m, 2H), 1.65 (m, 1H), 1.51 (m, 1H), 1.35 (q, J=12.0 Hz, 1H), 1.28-1.17 (m, 1H), 1.13 (dd, J=6.3, 2.5 Hz, 6H), 1.04-0.87 (m, 1H), 0.78 (d, J=6.4 Hz, 3H); $^{13}$C NMR (75 MHz, CDCl$_3$) δ 174.71 (s), 69.46 (d), 67.48 (d), 49.85 (d), 38.07 (t), 34.85 (t), 33.59 (d), 32.40 (t), 21.78 (q), 21.67 (q), 19.52 (q); GC-EIMS m/z (% rel. abundance) 200 (2), 182 (11), 140 (70), 95 (100);

ethanol is replaced with n-propanol to afford:

(1R*,2R*,5R*)-propyl 5-hydroxy-2-methylcyclohexanecarboxylate (F-3): IR (neat) 3392 (broad), 2931, 1731, 1136 cm$^{-1}$; $^1$H NMR (300 MHz, CDCl$_3$) δ 3.92 (t, J=6.6 Hz, 2H), 3.44 (tt, J=11.1, 4.1 Hz, 1H), 3.30 (br, 1H), 2.03-1.76 (m, 3H), 1.89-1.74 (m, 1H), 1.63 (m, 1H), 1.52 (m, 3H), 1.34 (q, J=12.0 Hz, 1H), 1.27-1.11 (m, 1H), 1.02-0.86 (m, 1H), 0.82 (t, J=7.4 Hz, 3H), 0.76 (d, J=6.4 Hz, 3H); $^{13}$C NMR (75 MHz, CDCl$_3$) δ 175.25 (s), 69.33 (d), 65.84 (t), 49.72 (d), 38.06 (t), 34.74 (t), 33.57 (d), 32.34 (t), 21.88 (t), 19.57 (q), 10.29 (q); GC-EIMS m/z (% rel. abundance) 200 (2), 182 (76), 141 (100), 95 (100); and ethanol is replaced with (±)-2-butanol to afford:

(1R*,2R*,5R*)-sec-butyl 5-hydroxy-2-methylcyclohexanecarboxylate (F-4) as a mixture of diastereomers: IR (neat) 3392 (broad), 2931, 1727, 1180 cm$^{-1}$; $^1$H NMR (300 MHz, CDCl$_3$) δ 4.83 (hept, J=6.2 Hz, 1H), 3.58 (m, 1H), 2.13-1.90 (m, 4H), 1.74 (dq, J=13.4, 3.6 Hz, 1H), 1.69-1.38 (m, 4H), 1.38-1.21 (m, 1H), 1.18 (sec-butyl CH$_3$ one diastereomer, d, J=2.4 Hz, 1.5H), 1.16 (sec-butyl CH$_3$ the other diastereomer, d, J=2.4 Hz, 1.5H), 1.04 (m, 1H), 0.93-0.81 (m, 6H); $^{13}$C NMR (75 MHz, CDCl$_3$) δ 174.85 (s), 174.81 (s), 72.02 (d), 71.99 (d), 69.37 (d), 50.03 (d), 49.95 (d), 38.14 (t), 38.08 (t), 34.78 (t), 33.53 (d), 33.42 (d), 32.36 (t), 32.32 (t), 28.66 (s), 19.52 (s), 19.45 (s), 19.33 (s), 9.65 (s), 9.60 (s) (doubling of some peaks was due to diastereomers due to the sec-butyl group); GC-EIMS m/z (% rel. abundance) 214 (1), 196 (2), 141 (68), 95 (100).

Ether Synthesis Method A: A mixture of (1R*,2R*,5R*)-ethyl 5-hydroxy-2-methylcyclohexanecarboxylate (F-1) (1.6 g, 8.6 mmol), Ag$_2$O (2.0 g, 8.4 mmol) and CH$_3$I (5.70 g, 40.2 mmol) in CH$_3$CN (20 mL) was stirred at room temperature. After 2 days, additional CH$_3$I (2.0 g, 14 mmol) was added. After 1 day, the reaction was filtered through Celite®, washed with MTBE, and concentrated. The crude oil was purified by silica gel chromatography eluting with a gradient of 0-30% EtOAc-hexanes to afford the title compound.

The following compounds were prepared from the corresponding alcohol according to Method A above:

(1R*,2R*,5R*)-isopropyl 5-hydroxy-2-methylcyclohexanecarboxylate;

(1R*,2R*,5R*)-propyl 5-hydroxy-2-methylcyclohexanecarboxylate; and (1R*,2R*,5R*)-sec-butyl 5-hydroxy-2-methylcyclohexanecarboxylate.

Ether Synthesis Method B: To a solution of the (1R*,2R*,5R*)-ethyl 5-hydroxy-2-methylcyclohexanecarboxylate (F-1) (930 mg, 4.99 mmol) and CH$_3$I (398 μL, 6.43 mmol) in DMF (4 mL) was added 60% NaH in mineral oil (200 mg, 5.00 mmol) in several portions. After 2 h, the reaction was quenched with saturated aqueous NH$_4$Cl (30 mL) and extracted with MTBE (3×25 mL). The organic layers were combined, washed with saturated aqueous NH$_4$Cl (3×20 mL) then brine (3×20 mL), dried (MgSO$_4$), filtered and concentrated. The crude oil was purified by silica gel chromatography, eluting with a gradient of 0-30% EtOAc-hexanes to afford the title compound.

The following compound was prepared from the corresponding alcohol according to method B above: (1R*,2R*,5R*)-propyl 5-hydroxy-2-methylcyclohexanecarboxylate.

Example 2: Synthesis of (1R*,2R*,5R*)-2,2,2-trifluoroethyl 5-methoxy-2-methylcyclohexanecarboxylate (2)

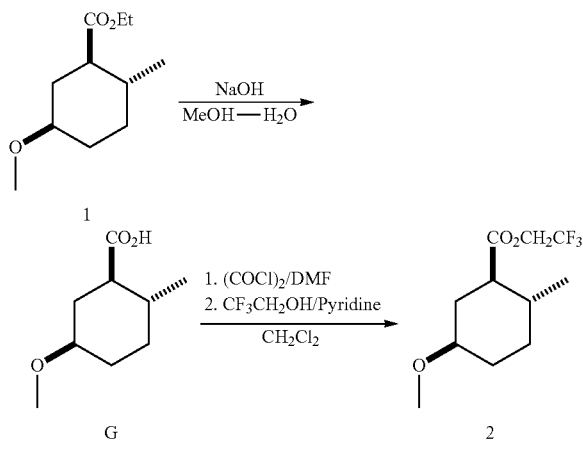

To a solution of (1R*,2R*,5R*)-ethyl 5-methoxy-2-methylcyclohexanecarboxylate (7.5 g, 37 mmol) in MeOH (50 mL) at 50° C. was added, in several portions, 4 N aqueous NaOH (25 mL, 100 mL). After 7 h, the mixture was cooled to room temperature. After 3 days, the mixture was diluted with brine (100 mL) and the excess MeOH removed in vacuo. The aqueous layer was extracted with MTBE (3×50 mL). The aqueous layer was, acidified with 3 N aqueous HCl (pH=2) and extracted with EtOAc (3×75 mL). The organic layers were combined, washed with brine (3×50 mL), dried (MgSO$_4$), filtered and concentrated to afford (1R*,2R*,5R*)-5-methoxy-2-methylcyclohexanecarboxylic acid (G): $^1$H NMR (300 MHz, CDCl$_3$) δ 3.35 (s, 3H), 3.24-3.07 (m, 1H), 2.35-2.21 (m, 1H), 2.13-1.94 (m, 2H), 1.80 (dq, J=13.5, 3.5 Hz, 1H), 1.75-1.56 (m, 1H), 1.48-1.35 (m, 1H), 1.34-1.20 (m, 1H), 1.13-0.97 (m, 1H), 0.95 (d, J=6.4 Hz, 3H).

To a chilled (0° C., ice salt bath) of (1R*,2R*,5R*)-5-methoxy-2-methylcyclohexanecarboxylic acid (G) (3.40 g, 19.7 mmol) in CH$_2$Cl$_2$ was added oxalyl chloride (2.33 mL, 27.5 mmol) followed by DMF (2.5 mL, 32.3 mmol) dropwise over a 30 min period. After 1 h, 2,2,2-trifluoroethanol (4.73 mL, 64.9 mmol) was added followed by pyridine (4.85 mL, 60.0 mmol). After 4 h, the reaction was diluted with saturated aqueous NH$_4$Cl (100 mL) and the excess CH$_2$Cl$_2$ was concentrated in vacuo. The aqueous layer was extracted with hexanes (3×50 mL). The combined organics were washed with saturated aqueous NH$_4$Cl (3×40 mL), 1 N aqueous HCl (3×40 mL), brine (2×40 mL), aqueous K$_2$CO$_3$ (2×40 mL), brine (2×40 mL), dried (MgSO$_4$) filtered and concentrated. The residue was purified on silica gel by column chromatography using a gradient of 0-20% EtOAc in hexanes to afford the title compound.

The following compounds were prepared from (1R*,2R*,5R*)-5-methoxy-2-methylcyclohexanecarboxylic acid according to the method describe in Example 2:

(1R*,2R*,5R*)-isopropyl 5-methoxy-2-methylcyclohexanecarboxylate; and (1R*,2R*,5R*)-sec-butyl 5-methoxy-2-methylcyclohexanecarboxylate.

Example 3: Synthesis of (1R*,2R*,5R*)-tert-butyl 5-methoxy-2-methylcyclohexanecarboxylate (3)

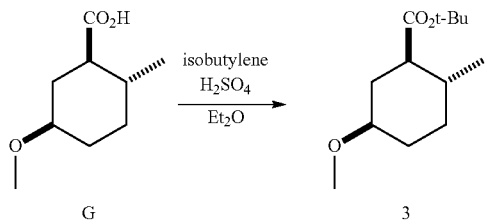 [SMILES: "Et2O" ; CO[C@@H]1CC[C@@H](C)[C@H](C(=O)O)C1 ; CO[C@@H]1CC[C@@H](C)[C@H](C(=O)OC(C)(C)C)C1]

To a chilled (−40° C.) solution of (1R*,2R*,5R*)-5-methoxy-2-methylcyclohexanecarboxylic acid (G) (6.50 g, 37.8 mmol) in diethyl ether was bubbled isobutylene gas (5.5 g, 98 mmol). To the solution was added concentrated sulfuric acid (5 drops) and the mixture was sealed in a 100-mL pressure reactor. The mixture was warmed to room temperature. After 18 h, the reaction was monitored by TLC (EtOAc:hexanes, 1:9) indicating starting material was still present. The mixture was cooled (−40° C.) and additional isobutylene gas (10.0 g, 196 mmol) was bubbled into the solution followed by additional sulfuric acid (15 drops). The mixture was sealed and stirred. After 3 days, the excess isobutylene was carefully vented and the mixture opened. The reaction was diluted with hexanes (150 mL) and washed with saturated aqueous $K_2CO_3$ (3×50 mL) until basic, brine (50 mL), dried ($MgSO_4$), filtered and concentrated. The residue was purified on silica gel by column chromatography using a gradient of 0-20% EtOAc in hexanes to afford the title compound.

Example 4: Synthesis of Intermediate (1R*,2R*,5R*)-ethyl 5-hydroxy-2-methylcyclohexanecarboxylate (F-1)

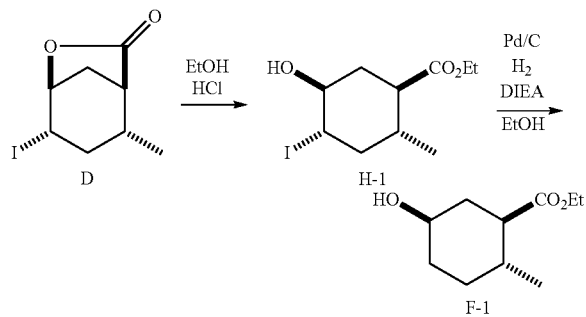

To absolute ethanol (35 mL) was added dropwise acetyl chloride (696 µL) to afford ethanolic-HCl. To the ethanolic-HCl solution was added (1S*,4S*,5S*)-4-iodo-6-oxa-bicyclo[3.2.1]octan-7-one (D) (8.80 g, 33.1 mmol), which initially stirred as a suspension. After 18 h, the reaction was made basic with $NaHCO_3$ (3 g) in water (80 mL) and the mixture was concentrated to remove excess ethanol. The aqueous residue was diluted with additional water and extracted with EtOAc (3×80 mL). The combined organic layers were washed with brine (80 mL), dried ($MgSO_4$), filtered and concentrated in vacuo to afford (1R*,2R*,4S*,5S*)-ethyl 5-hydroxy-4-iodo-2-methylcyclohexanecarboxylate (H-1) as a clear oil that solidified upon standing: m.p. 48.5-49.5° C.; $^1$H NMR (300 MHz, $CDCl_3$) δ 4.14 (q, J=7.1 Hz, 2H), 4.10-4.00 (m, 1H), 3.75-3.60 (m, 1H), 2.51-2.43 (m, 2H), 2.40 (broad, 1H), 2.28-2.09 (m, 1H), 1.96-1.68 (m, 2H), 1.70-1.45 (m, 1H), 1.25 (t, J=7.1 Hz, 3H), 0.92 (d, J=6.1 Hz, 3H); $^{13}$C NMR (75 MHz, $CDCl_3$) δ 173.91, 74.75, 60.48, 49.09, 45.63, 39.25, 36.42, 36.29, 18.83, 14.17.

A mixture of (1R*,2R*,4S*,5S*)-ethyl 5-hydroxy-4-iodo-2-methylcyclohexanecarboxylate (H-1) (1.07 g, 3.43 mmol), DIEA (1.0 mL, 5.7 mmol) and 10% Pd on carbon in ethanol (10 mL) was hydrogenated at 80 psi. After 18 h, the reaction was filtered through Celite®, washed with ethyl acetate, and then concentrated. The residue was diluted with saturated aqueous $NH_4Cl$ (30 mL) and extracted with ethyl acetate (3×25 mL). The combined organic layers were washed with brine (3×15 mL), dried ($MgSO_4$), filtered and concentrated to afford the title compound (F-1) that was identical by $^1$H NMR and GC-MS analysis to (1R*,2R*,5R*)-ethyl 5-hydroxy-2-methylcyclohexanecarboxylate (F-1) prepared in Example 1.

According to the method described in example 1, (1R*,2R*,5R*)-ethyl 5-hydroxy-2-methylcyclohexanecarboxylate (F-1) was converted to (1R*,2R*,5R*)-ethyl 5-methoxy-2-methylcyclohexanecarboxylate (1).

Assessment of Biological Properties: Compounds were assessed for the ability to attract Mediterranean fruit flies in an enclosed field cage.

Formulation of compounds on PVC disks: All test compounds were >95% pure by GC-MS, except for (1R*,2R*,5R*)-sec-butyl 5-methoxy-2-methylcyclohexanecarboxylate which was tested as a mixture of diastereomers due to the use of (±)-2-butanol in the formation of the ester, and were formulated as ~100 mg polymeric plugs containing ~40% by mass of a compound of Formula (I). A typical protocol dissolved polyvinyl chloride (PVC) (864 mg), dibutyl phthalate (DBP) (432 mg), dioctyl phthalate (DOP) (432 mg), (1R*,2R*,5R*)-ethyl 5-methoxy-2-methylcyclohexanecarboxylate (1) (1.152 g) in THF (8.64 g). The mixture was then pipetted (~400 mg) into respective porcelain wells. The THF was allowed to evaporate by warming the porcelain plate at 40° C. for 15 minutes, and then standing at room temperature until a constant weigh was achieved, to afford ~26 PVC-attractant disks with a mass of 104.0±3.4 mg, ($\bar{x}$±s).

Bioassays: Compounds were evaluated in screened field cages (3×3×2.5 meters) over a 24-hour period. Each field cage housed a single carousel, centered on the ceiling about 2 meters above the floor of the enclosure, which rotated (~1 revolution/min) 8 equally-spaced Jackson traps. A polymeric plug containing a test compound was placed in a small basket in each Jackson trap with a sticky insert to record the number of fly catches. Test compounds (6) were screened together with two "standard" attractants, TML (FarmaTech, USA) and (±)-CER-$B_1$ (prepared according to Khrimian, A., et al., Tetrahedron, 59: 5475 (2003)). A typical experiment (1) used 3 cages and began between 9-10 am each day, (2) TML and (±)-CER-B were arranged at two directly opposing poles of the carousel with 6 test compounds (3 on each side of TML and (±)-CER-$B_1$) randomly placed relative to the standards, (3) 6 randomly-selected patterns were tested over a 2-day period, with the same sequence of patterns repeated three times (days 1 & 2, days 3 & 4, and days 5 & 6) for a total of 3 replicates, (4) each 2-day period (days 1 & 2, days 3 & 4, and days 5 & 6) used a different cohort of 7-8 day old laboratory reared male Mediterranean fruit flies (n=3), and (5) 150 male Mediterranean fruit flies were released each morning per 24-h cage bioassay for a total of 900 flies per cohort and 2700 flies during the entire testing period. A fresh lure was used for each cage experiment (n=18). Mean fly catch numbers are depicted in the table below.

For each cohort, a single-factor ANOVAs was applied to test the null hypothesis that the mean capture of a particular lure across both days (six trials total, three each day) could be used to estimate attraction. The ANOVAs were not significant for any of the three cohorts, a finding that indicated significantly different daily differences were not observed for any of the lures, given a particular cohort. An additional single-factor ANOVAs was applied to test the null hypothesis that the grand mean capture of a particular lure could be used to estimate attraction, independent of the cohort. Again, none of the lure-respective ANOVAs were significant, a result that provided evidence to support congruence in the biological response across all cages, days, and cohorts. Also depicted in the table below, the grand mean capture ±2 pooled standard deviations (2 $s_{pooled}$) (Skoog, D. and Leary, J., Principles of Instrumental Analysis, John Wiley & Sons, Eds: New York, 1992). In general, the most attractive compounds in the above bioassay captured a similar (statistically equivalent) or greater number of flies relative to trimedlure.

| Structure[‡] | Name | Mean Catch per replicate |
|---|---|---|
| CO$_2$i-Pr | (1R*,2R*,5R*)-isopropyl 5-methoxy-2-methylcyclohexanecarboxylate | 64.7 ± 10.2a |
| CO$_2$n-Pr | (1R*,2R*,5R*)-propyl 5-methoxy-2-methylcyclohexanecarboxylate | 38.0 ± 9.7b |
| CO$_2$-sec-Bu | (1R*,2R*,5R*)-sec-butyl 5-methoxy-2-methylcyclohexanecarboxylate | 13.7 ± 3.0c |
| CO$_2$Et | (1R*,2R*,5R*)-ethyl 5-methoxy-2-methylcyclohexanecarboxylate | 91.0 ± 9.8d |
| CO$_2$t-Bu | (1R*,2R*,5R*)-tert-butyl 5-methoxy-2-methylcyclohexanecarboxylate | 9.0 ± 2.8c |
| CO$_2$CH$_2$CF$_3$ | (1R*,2R*,5R*)-2,2,2-trifluoroethyl 5-methoxy-2-methylcyclohexanecarboxylate | 94.0 ± 11.5d |

-continued

| Structure[‡] | Name | Mean Catch per replicate |
|---|---|---|
| Trimedlure[#] | tert-butyl 4- (and 5)-chloro-2-methylcyclohexanecarboxylate | 82.7 ± 11.3d |
| Ceralure-B$_1$[#] | (1R*,2R*,5R*)-ethyl 5-iodo-2-methylcyclohexanecarboxylate | 94.0 ± 10.7d |

Grand means followed by the same letter within a column within a test are not significantly different (P ≥0.05)
[#]Internal standards.
[‡]All compounds are racemic and diastereomerically pure, >95% by GC-MS except for trimedlure which is the commercial blend of isomers and (1R*,2R*,5R*)-sec-butyl 5-methoxy-2-methylcyclohexanecarboxylate which was tested as a mixture of diastereomers due to the use of (±)-2-butanol in the formation of the ester.

Method of Use: As one skilled in the art would expect, compounds of Formula (I) may be used as neat liquids, dissolved in inert solvents or oils, emulsified in water or a suitable carrier. Compounds of Formula (I) may be impregnated on dental wicks, rubber septa, paper or other absorbent materials. Compounds of Formula (I) may also be formulated in a polymer matrix such as PVC or a suitable polymer and optionally one or more plasticizers (i.e. DOP, DBP, or the like) (Fitzgerald, T. D., et al., Environ. Entomol., 2: 607 (1973); Hendricks, D. E., et al., Environ. Entomol., 16: 605 (1987); Sanders, C. J., Can. Entomol., 113:103 (1981)). Compounds of Formula (I) may be used alone or in combination with another compound of Formula (I), other known fruit fly attractants (i.e., TML, CER, CER-B$_1$, methyl eugenol, food-based lure such as ammonium acetate, trimethylamine hydrochloride, putrescine or the like), or fruit fly control agents (e.g., insecticides or the like). In general, compounds of the invention may be used in amounts determined by one skilled in the art depending on the application and duration of treatment (e.g., monitoring, eradication, male-annihilation). Some degree of routine dose optimization may be required to determine an optimal dosing level and pattern depending on the application. The chemical attractant may be administered in a range of 2-10 weeks on polymeric plugs or the like.

All of the references cited herein, including U.S. Patents, are incorporated by reference in their entirety. Also incorporated by reference in their entirety are the following references: USDA, APHIS, Fruit Fly Exclusion and Detection Programs 2011, Exotic Fruit Fly Strategic Plan FY2011-2015; Beroza, M., et al., J. Agric. Food Chem., 9: 361 (1961); Flath, R. A., et al., J. Chem. Ecol., 10: 2595 (1994); Warthen, J. D., et al., J. Chem. Ecol., 24: 1305 (1998); Tan, K. H., et al., Pheromones, Male Lures, and Trapping of Tephritid Fruit Flies; Epsky, N. D., et al., History and Development of Food-Based Attractants, IN: Trapping and the Detection, Control, and Regulation of Tephritid Fruit Flies: Lures, Area-Wide Programs, and Trade Implications, Shelly, T., et al., Eds., Springer: Dordrecht, 2014, pp. 15-118; DeMilo A. B., et al., J. Econ. Entomol., 87: 1494 (1994); McGovern, T. P., et al., J. Econ. Entomol., 81: 1052 (1988); Warthen, J. D., et al., J. Chem. Ecol., 20: 569 (1994); Jang, E., et al., J. Econ. Entomol., 103: 1586 (2010); Khrimian, A., et al., Tetrahedron, 59: 5475 (2003); Avery, J. W., et al., Tetrahedron Letters, 35: 9337 (1994), Khrimian, A., et al., Proceedings of 6th International Fruit Fly Symposium Stellenbosch, South Africa 279 (2002); DeMilo, A. B., Ceralure, IN: USDA-ARS Action Plan for Fruit Flies Research, Faust, R. M.; Coppedge, J. R. Eds., U.S. Department of Agriculture, Agricultural Research Service, 1992, pp. 11; Diels, O. and Alder, K., Liebigs Ann., 470: 62, (1929); House, H. O., et al., J. Org. Chem., 48:1643 (1983); Avery, J. W., et al., Tetrahedron Lett., 35: 9337 (1994); Mandal, P. K., et al., J. Org. Chem., 79: 8422 (2014); Raw, A. S., Jang, E. B., Patent No.: U.S. Pat. No. 6,375,943, Apr. 23, 2002; Clive, D. L. J., et al., J. Am. Chem. Soc., 112: 3018, (1990); Fitzgerald, T. D., et al., Environ. Entomol., 2: 607 (1973); Hendricks, D. E., et al., Environ. Entomol., 16: 605 (1987); Sanders, C. J., Can. Entomol., 113:103 (1981); Skoog, D. and Leary, J., Principles of Instrumental Analysis, John Wiley & Sons, Eds: New York, 1992.

The term "consisting essentially of" excludes additional method (or process) steps or composition components that substantially interfere with the intended activity of the method (or process) or composition, and can be readily determined by those skilled in the art (for example, from a consideration of this specification or practice of the invention disclosed herein).

The invention illustratively disclosed herein suitably may be practiced in the absence of any element (e.g., method (or process) steps or composition components) that is not specifically disclosed herein. Thus the specification includes disclosure by silence ("Negative Limitations In Patent Claims," AIPLA Quarterly Journal, Tom Brody, 41(1): 46-47 (2013):

. . . Written support for a negative limitation may also be argued through the absence of the excluded element in the specification, known as disclosure by silence . . .

Silence in the specification may be used to establish written description support for a negative limitation. As an example, in Ex parte Lin [No. 2009-0486, at 2, 6 (B.P.A.I. May 7, 2009)] the negative limitation was added by amendment . . . . In other words, the inventor argued an example that passively complied with the requirements of the negative limitation . . . was sufficient to provide support . . .

This case shows that written description support for a negative limitation can be found by one or more disclosures of an embodiment that obeys what is required by the negative limitation . . . .

Thus, in view of the above, there is described (in part) the following:

A compound of Formula (I)

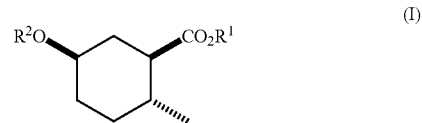

wherein $R^1$ is $C_{1-5}$ alkyl optionally substituted with 0-3 halogens, and $R^2$ is $C_{1-3}$ alkyl.

The above compound, wherein $R^1$ is methyl, ethyl, n-propyl, isopropyl, —$CH_2CF_3$, sec-butyl, or tert-butyl, and $R^2$ is methyl.

The above compound, wherein $R^1$ is ethyl, isopropyl, or —$CH_2CF_3$, and $R^2$ is methyl.

A composition comprising (or consisting essentially of or consisting of) at least one compound in the table below (which may be used as an attractant for Mediterranean fruit fly *Ceratitas capitata*), said compound having the relative stereochemistry depicted in the table below:

| Structure | Name | Data |
|---|---|---|
| $CO_2$i-Pr structure | (1R*,2R*,5R*)-isopropyl 5-methoxy-2-methylcyclohexanecarboxylate | IR (neat) 2978, 1728, 1101 cm$^{-1}$; $^1$H NMR (300 MHz, CDCl$_3$) δ 5.02 (hept, J = 6.2 Hz, 1H), 3.34 (s, 3H), 3.13 (m, 1H), 2.18 (m, 1H), 2.04 (m, 1H), 1.95 (m, 1H), 1.78 (m, 1H), 1.66 (m, 1H), 1.47-1.31 (m, 1H), 1.31-1.15 (m, partially obscured by doublets at 1.24 and 1.22 ppm, 1H), 1.23 (d, J = 6.3 Hz, 3H), 1.22 (d, J = 6.3 Hz, 3H), 0.88 (d, J = 6.4 Hz, 3H); $^{13}$C NMR (75 MHz, CDCl$_3$) δ 174.10, 78.21, 67.08, 55.50, 49.64, 34.57, 33.72, 32.22, 31.38, 21.64, 21.53, 19.43; GC-EIMS m/z (% rel. abundance) 214 (8), 184 (31). |
| $CO_2$n-Pr structure | (1R*,2R*,5R*)-propyl 5-methoxy-2-methylcyclohexanecarboxylate | IR (neat) 2934, 1732, 1100 cm$^{-1}$; $^1$H NMR (300 MHz, CDCl$_3$) δ 4.04 (td, J = 6.6, 0.7 Hz, 2H), 3.34 (s, 3H), 3.21-3.05 (m, 1H), 2.20 (ddd, J = 12.1, 6.1, 3.7 Hz, 1H), 2.11-1.92 (m, 2H), 1.78 (dq, J = 13.4, 3.5 Hz, 1H), 1.72-1.63 (m, 3H), 1.39 (td, J = 12.4, 11.2 Hz, 1H), 1.33-1.15 (m, 1H), 1.13-0.99 (m, 1H), 0.94 (t, J = 7.4 Hz, 3H), 0.89 (d, J = 6.4 Hz, 3H); $^{13}$C NMR (75 MHz, CDCl$_3$) δ 174.69, 78.21, 65.60, 55.51, 49.58, 34.65, 33.77, 32.23, 31.39, 21.87, 19.55, 10.23; GC-EIMS m/z (% rel. abundance) 214 (7), 184 (36). |
| $CO_2$ sec-butyl structure | (1R*,2R*,5R*)-sec-butyl 5-methoxy-2-methylcyclohexanecarboxylate | IR (neat) 2933, 1727, 1099 cm$^{-1}$; $^1$H NMR (300 MHz, CDCl$_3$) δ 4.85 (q, J = 6.2 Hz, 1H), 3.34 (s, 3H), 3.22-3.05 (m, 1H), 2.23-2.13 (m, 1H), 2.09-1.90 (m 2H), 1.83-1.72 (m, 1H), 1.72-1.46 (m, 3H), 1.46-1.32 (m, 1H), 1.31-1.22 (m, 1H), 1.19 and 1.18 (overlapping doublets due to racemic methyl group of the 2-methyl propyl group, J = 6.3 Hz, 3H), 1.11-0.94 (m, 1H), 0.92-0.86 (m, 6H); $^{13}$C NMR (75 MHz, CDCl$_3$) δ 174.00, 173.96, 78.08, 78.06, 71.46, 71.44, 55.31, 55.29, 49.71, 49.64, 34.65, 34.58, 33.61, 33.49, 32.10, 32.06, 31.26, 31.22, 28.49, 19.34, 19.21, 19.10, 9.41, 9.37 (doubling of some peaks is due to diastereomers due to the sec-butyl group); GC-EIMS m/z (% rel. abundance) 228 (6), 198 (8), 155 (36), 95 (100). |
| $CO_2$Et structure | (1R*,2R*,5R*)-ethyl 5-methoxy-2-methylcyclohexanecarboxylate | IR (neat) 2932, 1729, 1177, 1138, 1097 cm$^{-1}$; $^1$H NMR (300 MHz, CDCl$_3$) δ 4.07 (q, J = 15.0, 6.0 Hz, 2H), 3.26 (s, 3H), 3.12-2.99 (m, 1H), 2.16-2.07 (m, 1H), 2.01-1.86 (m, 2H), 1.77-1.66 (m, 1H), 1.64-1.50 (m, 1H), 1.37-1.23 (m, 1H), 1.18 (t, J = 7.1 Hz, 4H), 1.04-0.88 (m, 1H), 0.81 (d, J = 6.4 Hz, 3H); $^{13}$C NMR (75 MHz, CDCl$_3$) δ 174.92, 78.39, 60.18, 55.75, 49.66, 34.71, 33.92, 32.39, 31.57, 19.70, 14.26; GC-EIMS m/z (% rel. abundance) 200.1 (8), 170 (63). |
| $CO_2$t-Bu structure | (1R*,2R*,5R*)-tert-butyl 5-methoxy-2-methylcyclohexanecarboxylate | IR (neat) cm$^{-1}$ 2931, 1724, 1155, 1138, 1099; $^1$H NMR (300 MHz, CDCl$_3$) δ 3.34 (s, 3H), 3.18-3.05 (m, 1H), 2.23-2.13 (m, 1H), 2.09-1.96 (m, 1H), 1.86 (ddd, J = 12.6, 10.9, 3.3 Hz, 1H), 1.76 (dq, J = 13.4, 3.5 Hz, 1H), 1.68-1.53 (m, 1H), 1.44 (s, 9H), 1.41-1.30 (m, 1H), 1.30-1.20 (m, 1H), 1.10-0.97 (m, 1H), 0.89 (d, J = 6.4 Hz, 3H); $^{13}$C NMR (75 MHz, CDCl$_3$) δ 174.27, 80.01, 78.45, 77.58, 77.16, 76.73, 55.75, 50.67, 34.83, 33.97, 32.37, 31.58, 28.03, 19.62. |

-continued

| Structure | Name | Data |
|---|---|---|
| ![structure with CO2CH2CF3] | (1R*,2R*,5R*)-2,2,2-trifluoroethyl 5-methoxy-2-methylcyclohexanecarboxylate | IR (neat) cm$^{-1}$ 2934, 1752, 1272, 1127, 1098; $^1$H NMR (300 MHz, CDCl$_3$) δ 4.48 (q, J = 8.5 Hz, 2H), 3.34 (s, 3H), 3.14 (ddd, J = 15.0, 10.9, 4.0 Hz, 1H), 2.27-2.17 (m, 1H), 2.17-1.98 (m, 2H), 1.80 (dt, J = 13.3, 3.5 Hz, 1H), 1.75-1.61 (m, 1H), 1.41 (q, J = 12.0 Hz, 1H), 1.34-1.17 (m, 1H), 1.14-0.96 (m, 1H), 0.89 (d, J = 6.4 Hz, 3H); $^{13}$C NMR (75 MHz, CDCl$_3$) δ 173.29, 123.03 (q, J = 277.2 Hz), 78.16, 60.78, 60.29, 59.81, 59.32, 55.85, 49.21, 34.56, 33.92, 32.29, 31.45, 19.57; GC-EIMS m/z (% rel. abundance) 254 (3), 224 (41), 198 (48). | and optionally a carrier.

The above composition, wherein said composition contains a carrier.

The above composition, wherein said composition contains

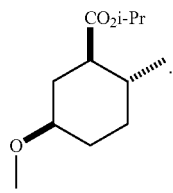

The above composition, wherein said composition does not contain

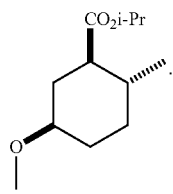

The above composition, wherein said composition contains

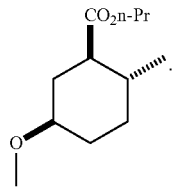

The above composition, wherein said composition does not contain

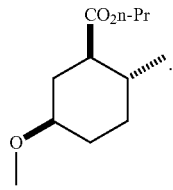

The above composition, wherein said composition contains

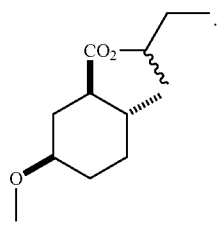

The above composition, wherein said composition does not contain

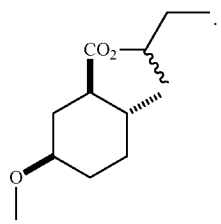

The above composition, wherein said composition contains

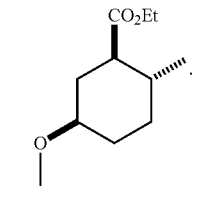

The above composition, wherein said composition does not contain

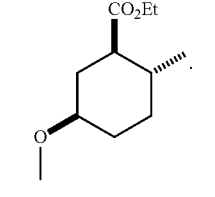

The above composition, wherein said composition contains

25

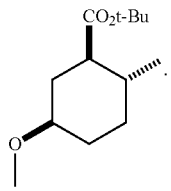 [SMILES: CO[C@@H]1CC[C@@H](C)[C@H](C(=O)OC(C)(C)C)C1]

The above composition, wherein said composition does not contain

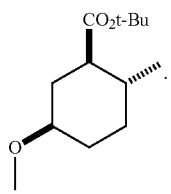 [SMILES: CO[C@@H]1CC[C@@H](C)[C@H](C(=O)OC(C)(C)C)C1]

The above composition, wherein said composition contains

26

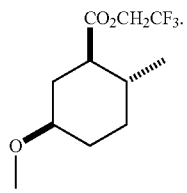

The above composition, wherein said composition does not contain

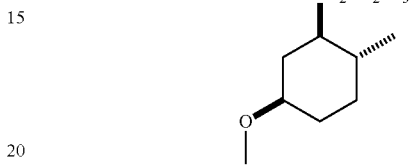

A method of attracting Mediterranean fruit fly, *Ceratitas capitata*, said method comprising (or consisting essentially of or consisting of) treating an object or area with a *Ceratitas capitata* attracting effective amount of a composition comprising (or consisting essentially of or consisting of) at least one compound in the table below, said compound having the relative stereochemistry depicted in the table below:

| Structure | Name | Data |
|---|---|---|
| CO$_2$i-Pr structure | (1R*,2R*,5R*)-isopropyl 5-methoxy-2-methylcyclohexanecarboxylate | IR (neat) 2978, 1728, 1101 cm$^{-1}$; $^1$H NMR (300 MHz, CDCl$_3$) δ 5.02 (hept, J = 6.2 Hz, 1H), 3.34 (s, 3H), 3.13 (m, 1H), 2.18 (m, 1H), 2.04 (m, 1H), 1.95 (m, 1H), 1.78 (m, 1H), 1.66 (m, 1H), 1.47-1.31 (m, 1H), 1.31-1.15 (m, partially obscured by doublets at 1.24 and 1.22 ppm, 1H), 1.23 (d, J = 6.3 Hz, 3H), 1.22 (d, J = 6.3 Hz, 3H), 0.88 (d, J = 6.4 Hz, 3H); $^{13}$C NMR (75 MHz, CDCl$_3$) δ 174.10, 78.21, 67.08, 55.50, 49.64, 34.57, 33.72, 32.22, 31.38, 21.64, 21.53, 19.43; GC-EIMS m/z (% rel. abundance) 214 (8), 184 (31). |
| CO$_2$n-Pr structure | (1R*,2R*,5R*)-propyl 5-methoxy-2-methylcyclohexanecarboxylate | IR (neat) 2934, 1732, 1100 cm$^{-1}$; $^1$H NMR (300 MHz, CDCl$_3$) δ 4.04 (td, J = 6.6, 0.7 Hz, 2H), 3.34 (s, 3H), 3.21-3.05 (m, 1H), 2.20 (ddd, J = 12.1, 6.1, 3.7 Hz, 1H), 2.11-1.92 (m, 2H), 1.78 (dq, J = 13.4, 3.5 Hz, 1H), 1.72-1.63 (m, 3H), 1.39 (td, J = 12.4, 11.2 Hz, 1H), 1.33-1.15 (m, 1H), 1.13-0.99 (m, 1H), 0.94 (t, J = 7.4 Hz, 3H), 0.89 (d, J = 6.4 Hz, 3H); $^{13}$C NMR (75 MHz, CDCl$_3$) δ 174.69, 78.21, 65.60, 55.51, 49.58, 34.65, 33.77, 32.23, 31.39, 21.87, 19.55, 10.23; GC-EIMS m/z (% rel. abundance) 214 (7), 184 (36). |
| sec-butyl ester structure | (1R*,2R*,5R*)-sec-butyl 5-methoxy-2-methylcyclohexanecarboxylate | IR (neat) 2933, 1727, 1099 cm$^{-1}$; $^1$H NMR (300 MHz, CDCl$_3$) δ 4.85 (q, J = 6.2 Hz, 1H), 3.34 (s, 3H), 3.22-3.05 (m, 1H), 2.23-2.13 (m, 1H), 2.09-1.90 (m, 2H), 1.83-1.72 (m, 1H), 1.72-1.46 (m, 3H), 1.46-1.32 (m, 1H), 1.31-1.22 (m, 1H), 1.19 and 1.18 (overlapping doublets due to racemic methyl group of the 2-methyl propyl group, J = 6.3 Hz, 3H), 1.11-0.94 (m, 1H), 0.92-0.86 (m, 6H); $^{13}$C NMR (75 MHz, CDCl$_3$) δ 174.00, 173.96, 78.08, 78.06, 71.46, 71.44, 55.31, 55.29, 49.71, 49.64, 34.65, 34.58, 33.61, 33.49, 32.10, 32.06, 31.26, 31.22, 28.49, 19.34, 19.21, 19.10, 9.41, 9.37 (doubling of some peaks is due to diastereomers due to the sec-butyl group); GC-EIMS m/z (% rel. abundance) 228 (6), 198 (8), 155 (36), 95 (100). |

-continued

| Structure | Name | Data |
|---|---|---|
| CO₂Et (structure) | (1R*,2R*,5R*)-ethyl 5-methoxy-2-methylcyclohexanecarboxylate | IR (neat) 2932, 1729, 1177, 1138, 1097 cm$^{-1}$; $^1$H NMR (300 MHz, CDCl$_3$) δ 4.07 (q, J = 15.0, 6.0 Hz, 2H), 3.26 (s, 3H), 3.12-2.99 (m, 1H), 2.16-2.07 (m, 1H), 2.01-1.86 (m, 2H), 1.77-1.66 (m, 1H), 1.64-1.50 (m, 1H), 1.37-1.23 (m, 1H), 1.18 (t, J = 7.1 Hz, 4H), 1.04-0.88 (m, 1H), 0.81 (d, J = 6.4 Hz, 3H); $^{13}$C NMR (75 MHz, CDCl$_3$) δ 174.92, 78.39, 60.18, 55.75, 49.66, 34.71, 33.92, 32.39, 31.57, 19.70, 14.26; GC-EIMS m/z (% rel. abundance) 200.1 (8), 170 (63). |
| CO₂t-Bu (structure) | (1R*,2R*,5R*)-tert-butyl 5-methoxy-2-methylcyclohexanecarboxylate | IR (neat) cm$^{-1}$ 2931, 1724, 1155, 1138, 1099; $^1$H NMR (300 MHz, CDCl$_3$) δ 3.34 (s, 3H), 3.18-3.05 (m, 1H), 2.23-2.13 (m, 1H), 2.09-1.96 (m, 1H), 1.86 (ddd, J = 12.6, 10.9, 3.3 Hz, 1H), 1.76 (dq, J = 13.4, 3.5 Hz, 1H), 1.68-1.53 (m, 1H), 1.44 (s, 9H), 1.41-1.30 (m, 1H), 1.30-1.20 (m, 1H), 1.10-0.97 (m, 1H), 0.89 (d, J = 6.4 Hz, 3H); $^{13}$C NMR (75 MHz, CDCl$_3$) δ 174.27, 80.01, 78.45, 77.58, 77.16, 76.73, 55.75, 50.67, 34.83, 33.97, 32.37, 31.58, 28.03, 19.62. |
| CO₂CH₂CF₃ (structure) | (1R*,2R*,5R*)-2,2,2-trifluoroethyl 5-methoxy-2-methylcyclohexanecarboxylate | IR (neat) cm$^{-1}$ 2934, 1752, 1272, 1127, 1098; $^1$H NMR (300 MHz, CDCl$_3$) δ 4.48 (q, J = 8.5 Hz, 2H), 3.34 (s, 3H), 3.14 (ddd, J = 15.0, 10.9, 4.0 Hz, 1H), 2.27-2.17 (m, 1H), 2.17-1.98 (m, 2H), 1.80 (dt, J = 13.3, 3.5 Hz, 1H), 1.75-1.61 (m, 1H), 1.41 (q, J = 12.0 Hz, 1H), 1.34-1.17 (m, 1H), 1.14-0.96 (m, 1H), 0.89 (d, J = 6.4 Hz, 3H); $^{13}$C NMR (75 MHz, CDCl$_3$) δ 173.29, 123.03 (q, J = 277.2 Hz), 78.16, 60.78, 60.29, 59.81, 59.32, 55.85, 49.21, 34.56, 33.92, 32.29, 31.45, 19.57; GC-EIMS m/z (% rel. abundance) 254 (3), 224 (41), 198 (48). | and optionally a carrier.

The above method, wherein said composition contains a carrier.

The above method, wherein said composition contains

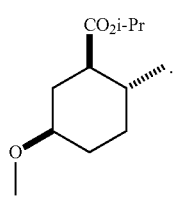

The above method, wherein said composition does not contain

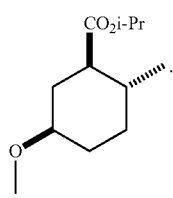

The above method, wherein said composition contains

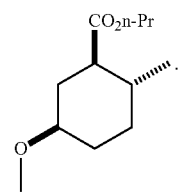

The above method, wherein said composition does not contain

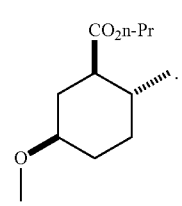

The above method, wherein said composition contains

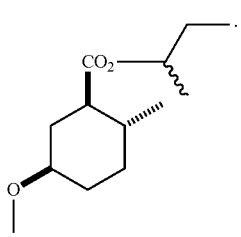

The above method, wherein said composition does not contain

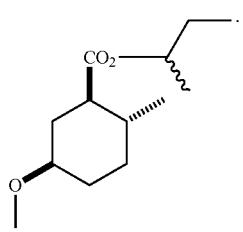

The above method, wherein said composition contains

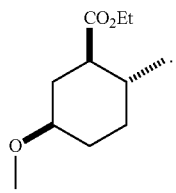

The above method, wherein said composition does not contain

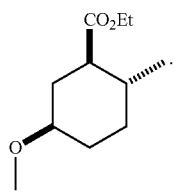

The above method, wherein said composition contains

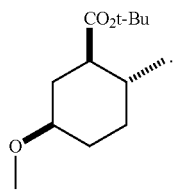 [SMILES: CO[C@@H]1CC[C@@H](C)[C@H](C(=O)OC(C)(C)C)C1]

The above method, wherein said composition does not contain

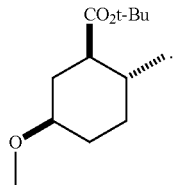 [SMILES: CO[C@@H]1CC[C@@H](C)[C@H](C(=O)OC(C)(C)C)C1]

The above method, wherein said composition contains

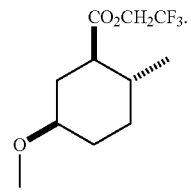

The above method, wherein said composition does not contain

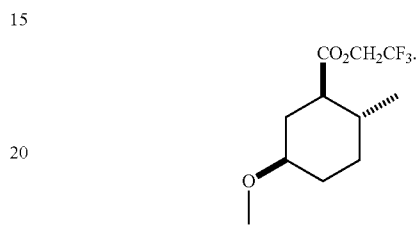

A method of making compounds of Formula (I)

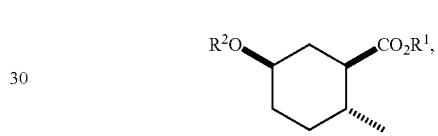

(I)

said method comprising (or consisting essentially of or consisting of):
reacting 1,3-butadiene of Formula (II)

II with (E)-crotonic acid of Formula (III)

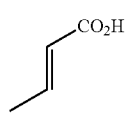

III to form siglure acid of Formula (IV)

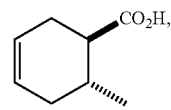

IV iodolactonization of siglure acid of Formula (IV) with KI, iodine, and $NaHCO_3$ in a solvent (e.g., water, tetrahydrofuran, dichloromethane or combinations thereof) to form the iodolactone of Formula (V)

V

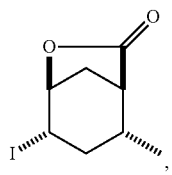

ring opening of the iodolactone of Formula (V) with a primary alcohol (e.g., methanol, ethanol or n-propanol) in the presence of catalytic acid (e.g., HCl or p-TsOH-H₂O) to form an ester of Formula (VI)

VI

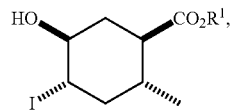

reducing the ester of Formula (VI) in a solvent (e.g., ethyl acetate (EtOAc) or ethanol (EtOH)) using a catalyst (e.g., palladium on carbon, platinum oxide (Adam's catalyst), Raney nickel or palladium hydroxide) in the presence of hydrogen at a suitable pressure and an amine base (e.g., triethylamine, DIEA or pyridine) to form the compound of Formula (VII)

VII

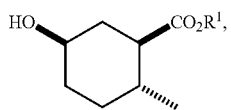

and etherification of the compound of Formula (VII) in a solvent (e.g., dimethylformamide (DMF) or acetonitrile) using an alkyl halide (e.g., iodomethane) and a base (e.g., NaH or silver (I) oxide to form the compound of Formula (I) wherein R² is methyl.

A method of making compounds of Formula I

I

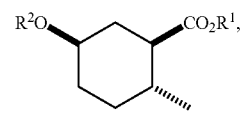

said method comprising (or consisting essentially of or consisting of):

reducing the iodolactone of Formula (V)

V

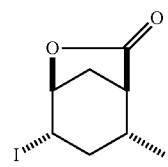

under hydrogenation conditions in a solvent (e.g., ethyl acetate or ethanol) using a catalyst (e.g., palladium on carbon, platinum oxide (Adam's catalyst), palladium hydroxide or Raney® nickel) in the presence of hydrogen at a suitable pressure and an amine base (e.g., triethylamine, DIEA or pyridine) or reducing the iodolactone of Formula (V) using tri-n-butyl tin hydride and a radical initiator (e.g., azobisisobutyronitrile (AIBN)) to form the lactone of Formula (VIII)

VIII

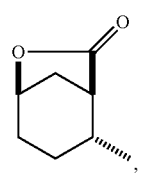

ring-opening of the lactone of Formula (VIII) with an alcohol (e.g., ethanol, propanol isopropanol, (±)-2-butanol (sec-butylalchol)) in the presence of a base (e.g., NaH or K₂CO₃) or an acid (e.g., HCl (g), ethanolic-HCl)) to form an ester of Formula (VII)

VII

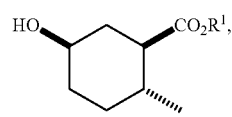

and etherification of the compound of Formula (VII) in a solvent (e.g., dimethylformamide (DMF) or acetonitrile) using an alkyl halide (e.g., iodomethane) and a base (e.g., NaH) or silver (I) oxide to form the compound of Formula (I).

A method of making compounds of Formula I

I

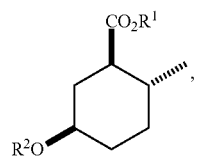

said method comprising (or consisting essentially of or consisting of):

hydrolyzing an ester of Formula (IX)

IX

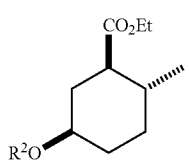

under basic conditions in a solvent (e.g., methanol) using a base (e.g., sodium, potassium or lithium hydroxide) in water to afford a carboxylic acid of Formula (X)

X

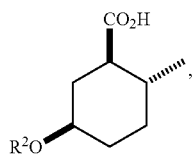

esterification of the carboxylic acid of Formula (X) with SOCl$_2$ or oxalyl chloride-DMF followed by an alcohol (e.g., ethanol, propanol, isopropanol, (±)-2-butanol (sec-butyl alcohol), 2,2,2-trifluoroethanol and the like) in the presence of a base (e.g., pyridine) to form a compound of Formula (I).

A method of making compounds of Formula I

I

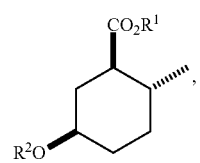

said method comprising (or consisting essentially of or consisting of):

hydrolyzing an ester of Formula (I) under basic conditions in a solvent (e.g., methanol) using a base (e.g., sodium, potassium or lithium hydroxide) in water to afford a carboxylic acid of Formula (IX)

IX

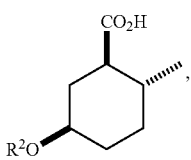

and treating the carboxylic acid of Formula (IX) with isobutylene in the presence of an acid catalyst (e.g., sulfuric acid) to form an ester of Formula (I) where R$^1$ is tert-butyl.

A compound comprising at least one compound in the table below (which may be used as an attractant for Mediterranean fruit fly, *Ceratitas capitata*), said compound having the relative stereochemistry depicted in the table below:

| Structure | Name |
| --- | --- |
| CO$_2$i-Pr | (1R*,2R*,5R*)-isopropyl 5-methoxy-2-methylcyclohexanecarboxylate |
| CO$_2$n-Pr | (1R*,2R*,5R*)-propyl 5-methoxy-2-methylcyclohexanecarboxylate |
| CO$_2$-sec-butyl | (1R*,2R*,5R*)-sec-butyl 5-methoxy-2-methylcyclohexanecarboxylate |
| CO$_2$Et | (1R*,2R*,5R*)-ethyl 5-methoxy-2-methylcyclohexanecarboxylate |
| CO$_2$t-Bu | (1R*,2R*,5R*)-tert-butyl 5-methoxy-2-methylcyclohexanecarboxylate |
| CO$_2$CH$_2$CF$_3$ | (1R*,2R*,5R*)-2,2,2-trifluoroethyl 5-methoxy-2-methylcyclohexanecarboxylate. |

The compound above, comprising at least one compound in the table below (which may be used as an attractant for Mediterranean fruit fly, *Ceratitas capitata*), said compound having the relative stereochemistry depicted in the table below:

| Structure | Name |
| --- | --- |
| CO$_2$Et | (1R*,2R*,5R*)-ethyl 5-methoxy-2-methylcyclohexanecarboxylate |
| CO$_2$CH$_2$CF$_3$ | (1R*,2R*,5R*)-2,2,2-trifluoroethyl 5-methoxy-2-methylcyclohexanecarboxylate. |

The compound above, comprising at least one compound in the table below (which may be used as an attractant for Mediterranean fruit fly, *Ceratitas capitata*), said compound having the relative stereochemistry depicted in the table below:

| Structure | Name |
|---|---|
| (structure with CO₂i-Pr) | (1R*,2R*,5R*)-isopropyl 5-methoxy-2-methylcyclohexanecarboxylate |
| (structure with CO₂n-Pr) | (1R*,2R*,5R*)-propyl 5-methoxy-2-methylcyclohexanecarboxylate. |

The compound above, comprising at least one compound in the table below (which may be used as an attractant for Mediterranean fruit fly, *Ceratitas capitata*), said compound having the relative stereochemistry depicted in the table below:

| Structure | Name |
|---|---|
| (structure with CO₂ sec-butyl) | (1R*,2R*,5R*)-sec-butyl 5-methoxy-2-methylcyclohexanecarboxylate |
| (structure with CO₂t-Bu) | (1R*,2R*,5R*)-tert-butyl 5-methoxy-2-methylcyclohexanecarboxylate. |

The above compound, wherein said compound is (structure with CO₂i-Pr)

The above compound, wherein said compound is not

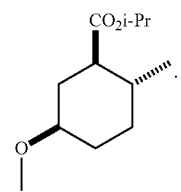

The above compound, wherein said compound is

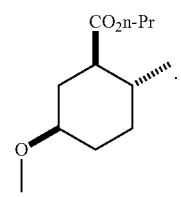

The above compound, wherein said compound is not

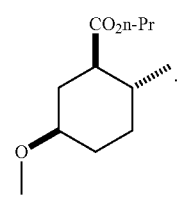

The above compound, wherein said compound is

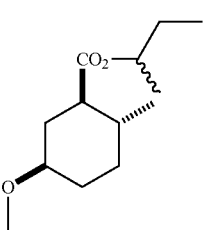

The above compound, wherein said compound is not

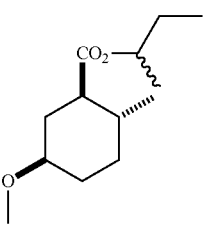

The above compound, wherein said compound is

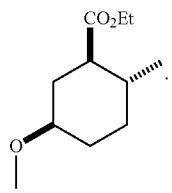

The above compound, wherein said compound is not

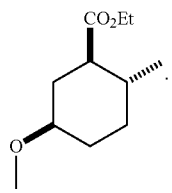

The above compound, wherein said compound is

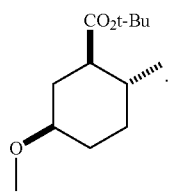 [SMILES: CO[C@@H]1CC[C@@H](C)[C@H](C(=O)OC(C)(C)C)C1]

The above compound, wherein said compound is not

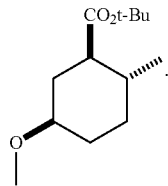 [SMILES: CO[C@@H]1CC[C@@H](C)[C@H](C(=O)OC(C)(C)C)C1]

The above compound, wherein said compound is

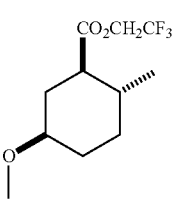

The above compound, wherein said compound is not

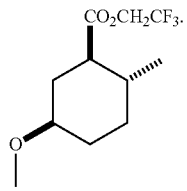

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. A compound of Formula (I)

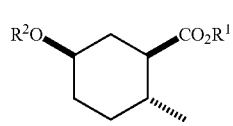

(I)

wherein $R^1$ is $C_{1-5}$ alkyl optionally substituted with 0-3 halogens, and $R^2$ is $C_{1-3}$ alkyl.

2. The compound of claim 1, wherein $R^1$ is methyl, ethyl, n-propyl, isopropyl, —$CH_2CF_3$, sec-butyl, or tert-butyl, and $R^2$ is methyl.

3. The compound of claim 1, wherein $R^1$ is ethyl, isopropyl, or —$CH_2CF_3$, and $R^2$ is methyl.

4. A composition comprising at least one compound in the table below, said compound having the relative stereochemistry depicted in the table below:

| Structure | Name |
|---|---|
| 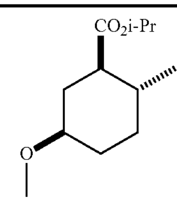 | (1R*,2R*,5R*)-isopropyl 5-methoxy-2-methylcyclohexanecarboxylate |
| 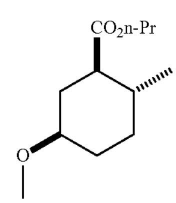 | (1R*,2R*,5R*)-propyl 5-methoxy-2-methylcyclohexanecarboxylate |
| 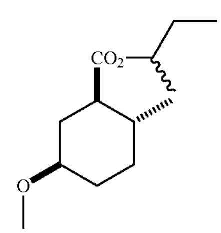 | (1R*,2R*,5R*)-sec-butyl 5-methoxy-2-methylcyclohexanecarboxylate |

| Structure | Name |
|---|---|
| (structure with CO₂Et) | (1R*,2R*,5R*)-ethyl 5-methoxy-2-methylcyclohexanecarboxylate |
| (structure with CO₂t-Bu) | (1R*,2R*,5R*)-tert-butyl 5-methoxy-2-methylcyclohexanecarboxylate |
| (structure with CO₂CH₂CF₃) | (1R*,2R*,5R*)-2,2,2-trifluoroethyl 5-methoxy-2-methylcyclohexanecarboxylate | and optionally a carrier.

5. The composition according to claim 4, wherein said composition contains a carrier.

6. A method of attracting Mediterranean fruit fly, *Ceratitas capitata*, said method comprising treating an object or area with a *Ceratitas capitata* attracting effective amount of a composition comprising at least one compound in the table below, said compound having the relative stereochemistry depicted in the table below:

| Structure | Name |
|---|---|
| (structure with CO₂i-Pr) | (1R*,2R*,5R*)-isopropyl 5-methoxy-2-methylcyclohexanecarboxylate |
| (structure with CO₂n-Pr) | (1R*,2R*,5R*)-propyl 5-methoxy-2-methylcyclohexanecarboxylate |
| (structure with CO₂ sec-butyl) | (1R*,2R*,5R*)-sec-butyl 5-methoxy-2-methylcyclohexanecarboxylate |

| Structure | Name |
|---|---|
| (structure with CO₂Et) | (1R*,2R*,5R*)-ethyl 5-methoxy-2-methylcyclohexanecarboxylate |
| (structure with CO₂t-Bu) | (1R*,2R*,5R*)-tert-butyl 5-methoxy-2-methylcyclohexanecarboxylate |
| (structure with CO₂CH₂CF₃) | (1R*,2R*,5R*)-2,2,2-trifluoroethyl 5-methoxy-2-methylcyclohexanecarboxylate | and optionally a carrier.

7. The method according to claim 6, wherein said composition contains a carrier.

8. A method of making compounds of Formula (I)

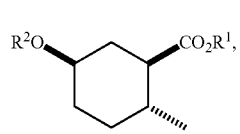

(I)

said method comprising:
reacting 1,3-butadiene of Formula (II)

II with (E)-crotonic acid of Formula (III)

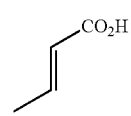

III to form siglure acid of Formula (IV)

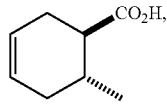   IV iodolactonization of siglure acid of Formula (IV) with KI, iodine, and NaHCO$_3$ in a solvent to form the iodolactone of Formula (V)

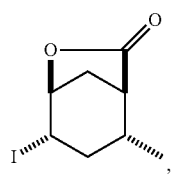   V ring opening of the iodolactone of Formula (V) with a primary alcohol in the presence of catalytic acid to form an ester of Formula (VI)

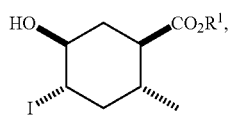   VI reducing the ester of Formula (VI) in a solvent using a catalyst in the presence of hydrogen and an amine base to form the compound of Formula (VII)

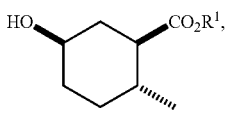   VII and etherification of the compound of Formula (VII) in a solvent using an alkyl halide and a base to form the compound of Formula (I) wherein R$^2$ is methyl.

9. A method of making compounds of Formula I

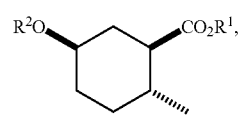   I said method comprising:
reducing the iodolactone of Formula (V)

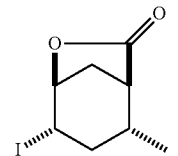   V in a solvent using a catalyst in the presence of hydrogen and an amine base or reducing the iodolactone of Formula (V) using tri-n-butyl tin hydride and a radical initiator to form the lactone of Formula (VIII)

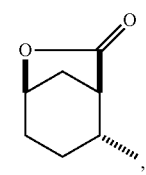   VIII ring-opening of the lactone of Formula (VIII) with an alcohol in the presence of a base or an acid to form an ester of Formula (VII)

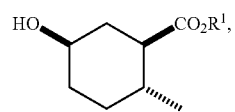   VII and etherification of the compound of Formula (VII) in a solvent and a base or silver (I) oxide to form the compound of Formula (I).

10. A method of making compounds of Formula I

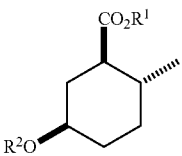   I said method comprising:
hydrolyzing an ester of Formula (IX)

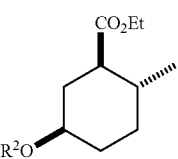   IX under basic conditions in water and a co-solvent to afford a carboxylic acid of Formula (X)

X

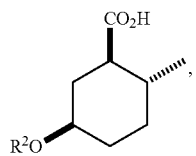

and
  esterification of the carboxylic acid of Formula (X) with SOCl$_2$ or oxalyl chloride-DMF followed by an alcohol in the presence of a base to form a compound of Formula (I).

11. A method of making compounds of Formula I

I

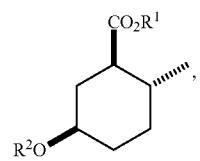

said method comprising:
  hydrolyzing an ester of Formula (IX)

IX

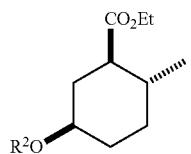

under basic conditions in water in a solvent using a base to afford a carboxylic acid of Formula (X)

X

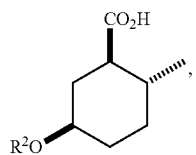

and
  treating the carboxylic acid of Formula (X) with isobutylene in the presence of an acid catalyst to form an ester of Formula (I) where R$^1$ is tert-butyl.

12. A compound comprising at least one compound in the table below, said compound having the relative stereochemistry depicted in the table below:

| Structure | Name |
|---|---|
| CO$_2$i-Pr (cyclohexane structure) | (1R*,2R*,5R*)-isopropyl 5-methoxy-2-methylcyclohexanecarboxylate |
| CO$_2$n-Pr (cyclohexane structure) | (1R*,2R*,5R*)-propyl 5-methoxy-2-methylcyclohexanecarboxylate |
| CO$_2$ sec-butyl (cyclohexane structure) | (1R*,2R*,5R*)-sec-butyl 5-methoxy-2-methylcyclohexanecarboxylate |
| CO$_2$Et (cyclohexane structure) | (1R*,2R*,5R*)-ethyl 5-methoxy-2-methylcyclohexanecarboxylate |
| CO$_2$t-Bu (cyclohexane structure) | (1R*,2R*,5R*)-tert-butyl 5-methoxy-2-methylcyclohexanecarboxylate |
| CO$_2$CH$_2$CF$_3$ (cyclohexane structure) | (1R*,2R*,5R*)-2,2,2-trifluoroethyl 5-methoxy-2-methylcyclohexanecarboxylate. |

13. The compound of claim 12, comprising at least one compound in the table below, said compound having the relative stereochemistry depicted in the table below:

| Structure | Name |
|---|---|
| CO$_2$Et (cyclohexane structure) | (1R*,2R*,5R*)-ethyl 5-methoxy-2-methylcyclohexanecarboxylate |
| CO$_2$CH$_2$CF$_3$ (cyclohexane structure) | (1R*,2R*,5R*)-2,2,2-trifluoroethyl 5-methoxy-2-methylcyclohexanecarboxylate. |

14. The compound of claim 12, comprising at least one compound in the table below, said compound having the relative stereochemistry depicted in the table below:

| Structure | Name |
|---|---|
| (cyclohexane with CO₂i-Pr, methyl, and OMe substituents) | (1R*,2R*,5R*)-isopropyl 5-methoxy-2-methylcyclohexanecarboxylate |
| (cyclohexane with CO₂n-Pr, methyl, and OMe substituents) | (1R*,2R*,5R*)-propyl 5-methoxy-2-methylcyclohexanecarboxylate. |

15. The compound of claim 12, comprising at least one compound in the table below, said compound having the relative stereochemistry depicted in the table below:

| Structure | Name |
|---|---|
| (cyclohexane with CO₂-sec-butyl, methyl, and OMe substituents) | (1R*,2R*,5R*)-sec-butyl 5-methoxy-2-methylcyclohexanecarboxylate |
| (cyclohexane with CO₂t-Bu, methyl, and OMe substituents) | (1R*,2R*,5R*)-tert-butyl 5-methoxy-2-methylcyclohexanecarboxylate. |

\* \* \* \* \*